US012681014B2

(12) United States Patent
Ren

(10) Patent No.: US 12,681,014 B2
(45) Date of Patent: Jul. 14, 2026

(54) SYSTEMS, DEVICES, AND METHODS FOR AMPLIFYING SIGNALS OF A LATERAL FLOW ASSAY

(71) Applicant: Becton, Dickinson and Company, Franklin Lakes, NJ (US)

(72) Inventor: Huimiao Ren, San Diego, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1452 days.

(21) Appl. No.: 17/123,995

(22) Filed: Dec. 16, 2020

(65) Prior Publication Data

US 2021/0156856 A1     May 27, 2021

Related U.S. Application Data

(63) Continuation of application No. PCT/US2019/035725, filed on Jun. 6, 2019.

(Continued)

(51) Int. Cl.
G01N 33/543     (2006.01)
G01N 21/77     (2006.01)
G01N 21/84     (2006.01)

(52) U.S. Cl.
CPC ....... *G01N 33/54388* (2021.08); *G01N 21/77* (2013.01); *G01N 21/8483* (2013.01); *G01N 2021/7759* (2013.01)

(58) Field of Classification Search
CPC ............. G01N 33/54388; G01N 21/77; G01N 21/8483; G01N 2021/7759; G01N 33/558; G01N 33/54387; G01N 33/54389; B01L 2300/0825

USPC ....... 422/400, 401, 420, 421, 425, 426, 430; 435/287.7, 287.9, 969, 970, 805, 810; 436/169, 170, 514, 518, 530, 810
See application file for complete search history.

(56) References Cited

U.S. PATENT DOCUMENTS 4,868,131 A     9/1989   Hiratsuka
5,395,754 A     3/1995   Lambotte et al.
(Continued)

FOREIGN PATENT DOCUMENTS

CN     101002096 A     7/2007
CN     104105965 A     12/2008
(Continued)

OTHER PUBLICATIONS

Qi et al., Dual-quantum-dots-labeled lateral flow strip rapidly quantifies procalcitonin and C-reactive protein. Nanoscale Res Letts. Dec. 2016;11(1): 1-8.

(Continued)

*Primary Examiner* — Christopher L Chin
(74) *Attorney, Agent, or Firm* — KNOBBE, MARTENS, OLSON & BEAR, LLP

(57) ABSTRACT

Lateral flow assay devices, systems, and methods described herein detect analyte present in a sample in low quantity or at low concentration by amplifying a signal generated at a detection zone. The generated signal can exceed a detection threshold of a measurement system and increase the sensitivity of the lateral flow assay devices, systems, and methods. In one aspect, the lateral flow device includes a signal-amplification conjugate that binds to a complex bound to immobilized capture agent in the detection zone, causing a chain reaction of binding events in the detection zone that result in an amplification of the signal generated in the detection zone.

25 Claims, 6 Drawing Sheets

Related U.S. Application Data

(60) Provisional application No. 62/686,606, filed on Jun. 18, 2018.

(56) References Cited

U.S. PATENT DOCUMENTS

| | | | |
|---|---|---|---|
| 5,656,503 A | 8/1997 | May et al. |
| 6,183,972 B1 | 2/2001 | Kuo et al. |
| 6,306,642 B1 | 10/2001 | Nelson et al. |
| 6,593,085 B1 | 7/2003 | Barnett et al. |
| 6,924,153 B1 | 8/2005 | Boehringer et al. |
| 7,410,808 B1 | 8/2008 | Saul et al. |
| 7,439,079 B2 | 10/2008 | Song et al. |
| 7,651,841 B2 | 1/2010 | Song et al. |
| 8,603,835 B2 | 12/2013 | Esfandiari |
| 8,709,792 B2 | 4/2014 | Saul et al. |
| 9,482,675 B1 | 11/2016 | Lovell et al. |
| 2001/0026920 A1 | 10/2001 | Chandler et al. |
| 2003/0119204 A1 | 6/2003 | Wei et al. |
| 2005/0221504 A1 | 10/2005 | Petruno et al. |
| 2006/0029976 A1 | 2/2006 | McVicker et al. |
| 2006/0127886 A1 | 6/2006 | Kaylor et al. |
| 2006/0134803 A1 | 6/2006 | Esfandiari |
| 2006/0160078 A1 | 7/2006 | Cardy et al. |
| 2006/0246601 A1 | 11/2006 | Song et al. |
| 2007/0224701 A1 | 9/2007 | Rosenstein |
| 2007/0243630 A1 | 10/2007 | Boehringer et al. |
| 2008/0118911 A1 | 5/2008 | Hermann |
| 2008/0254444 A1 | 10/2008 | Esfandiari |
| 2008/0310998 A1 | 12/2008 | Lamotte |
| 2009/0180927 A1 | 7/2009 | Petruno et al. |
| 2009/0196792 A1 | 8/2009 | Raj et al. |
| 2009/0246886 A1 | 10/2009 | Buck |
| 2009/0253219 A1 | 10/2009 | Bauer et al. |
| 2010/0062543 A1 | 3/2010 | Song et al. |
| 2010/0068826 A1 | 3/2010 | Gokhan |
| 2011/0086359 A1 | 4/2011 | Babu et al. |
| 2011/0136258 A1 | 6/2011 | Sambursky et al. |
| 2011/0229913 A1 | 9/2011 | Bae et al. |
| 2011/0275542 A1 | 11/2011 | Eden et al. |
| 2012/0083047 A1 | 4/2012 | Nazareth et al. |
| 2012/0129272 A1 | 5/2012 | Petruno et al. |
| 2013/0084580 A1 | 4/2013 | Wada et al. |
| 2013/0137598 A1 | 5/2013 | Verschoor et al. |
| 2013/0244314 A1 | 9/2013 | Yuki et al. |
| 2014/0134653 A1 | 5/2014 | Ding et al. |
| 2014/0170642 A1 | 6/2014 | Huang et al. |
| 2014/0377879 A1 | 12/2014 | Sharrock et al. |
| 2015/0080250 A1 | 3/2015 | Shi et al. |
| 2015/0293085 A1 | 10/2015 | Anderberg et al. |
| 2015/0323534 A1 | 11/2015 | Egan et al. |
| 2016/0084843 A1 | 3/2016 | Abendroth et al. |
| 2016/0153993 A1 | 6/2016 | Eden et al. |
| 2016/0223536 A1 | 8/2016 | Johnson et al. |
| 2016/0266119 A1 | 9/2016 | Sambursky et al. |
| 2016/0291010 A1 | 10/2016 | Kim et al. |
| 2017/0074874 A1 | 3/2017 | Hunter et al. |
| 2020/0209235 A1 | 7/2020 | Guckenberger |
| 2020/0292542 A1 | 9/2020 | Liu |
| 2020/0348296 A1 | 11/2020 | Ren et al. |
| 2020/0348298 A1 | 11/2020 | Ren et al. |
| 2021/0405044 A1 | 12/2021 | Yang et al. |

FOREIGN PATENT DOCUMENTS

| | | | |
|---|---|---|---|
| CN | 104364652 A | 2/2015 |
| CN | 105723220 A | 6/2016 |
| EP | 0254117 A2 | 1/1988 |
| EP | 0297292 A2 | 1/1989 |
| EP | 0696735 A1 | 2/1996 |
| EP | 0987551 A2 | 3/2000 |
| GB | 2443694 A | 5/2008 |
| JP | 2004500569 A | 1/2004 |
| JP | 2005010001 A | 1/2005 |
| JP | 2006208386 A | 8/2006 |
| JP | 2008-539424 | 11/2008 |
| JP | 2009294116 A | 12/2009 |
| JP | 2010-512537 | 4/2010 |
| JP | 2010523996 A | 7/2010 |
| JP | 2011209140 A | 10/2011 |
| JP | 2013-513113 | 4/2013 |
| JP | 2013171024 A | 9/2013 |
| JP | 2013213803 A | 10/2013 |
| JP | 2016500154 A | 1/2016 |
| JP | 2016520827 A | 7/2016 |
| JP | 2017015532 A | 1/2017 |
| JP | 2017515130 A | 6/2017 |
| JP | 2017181368 A | 10/2017 |
| WO | WO 1998/023958 A1 | 6/1998 |
| WO | WO 2008/073222 | 6/2008 |
| WO | WO 2010/061992 | 6/2010 |
| WO | WO 2010/132453 | 11/2010 |
| WO | WO 2011/069031 | 6/2011 |
| WO | WO 2013/088429 | 6/2013 |
| WO | WO 2011/125877 | 7/2013 |
| WO | WO 2013/112216 | 8/2013 |
| WO | WO 2013/117746 | 8/2013 |
| WO | WO 2013/132338 | 9/2013 |
| WO | WO 2012/043746 | 2/2014 |
| WO | WO 2014/070686 | 5/2014 |
| WO | WO 2014/078679 | 5/2014 |
| WO | WO 2015/109255 | 7/2015 |
| WO | WO 2017/221255 | 12/2017 |
| WO | WO 2018/011795 | 1/2018 |
| WO | WO 2019/005694 | 1/2019 |
| WO | WO 2019/112944 | 6/2019 |

OTHER PUBLICATIONS

Wiriyachaiporn et al., Dual-layered and double-targeted nanogold based lateral flow immunoassay for influenza virus. Microchim Acta. Jan. 2015;182:85-93.

Rey et al., Mitigating the hook effect in lateral flow sandwich immunoassays using real-time reaction kinetics. Analy Chem. (May 2017) 89(9): 5095-5100.

Vashist et al., Bioanalytical advances in assays for C-reactive protein, Biotech Advances (Dec. 2015) 34(3): 272-290.

Eden et al., Diagnostic accuracy of a Trail, IP-10 and CRP combination for discriminating bacterial and viral etiologies at the emergency department. J Infect. Aug. 1, 2016;73(2):177-180.

Oved et al., A novel host-proteome signature for distinguishing between acute bacterial and viral infections. PloS One Mar. 18, 2015;10(3):e0120012 in 18 pages.

Oved et al., Tumor necrosis factor-related apoptosis-inducing ligand protein as a marker for disease severity in patients with acute infection. Open Forum Infect Diseases Dec. 1, 2016;3(Suppl 1):236.

Wang et al., Monoclonal antibody against CXCL-10/IP-10 ameliorates influenza A (H1N1) virus induced acute lung injury. Cell Res. Apr. 2013;23(4):577-580.

Choi et al., A dual gold nanoparticle conjugate-based lateral flow assay (LFA) method for the analysis of troponin I., Biosens Bioelectron. 2010, 25(8):1999-2002.

Hu et al., Sensitive and Quantitative Detection of C-Reaction Protein Based on Immunofluorescent Nanospheres Coupled with Lateral Flow Test Strip. Anal Chem. (Jun. 2016) 88(12):6577-6584.

Huttunen et al., Residual nanoparticle label immunosensor for wash-free C-reactive protein detection in blood. Biosens Bioelectron., 2016, 83:54-59.

Melin et al., A multiplexed point-of-care assay for C-reaction protein and N-terminal pro-brain natriuretic peptide, Analyt Biochem., 2011, 409:7-13.

Nanocomposix, Lateral Flow Assay Development Guide, Version 1.1., 2016, Published May 2017, Product Handbook [retrieved Jul. 23, 2019] URL: https://cdn.shopify.com/s/files/1/0257/8237/files/BioReady_Lateral_Flow_Handbook_v-1.1.pdf.

Razo et al., Double-enhanced lateral flow immunoassay for potato virus X based on a combination of magnetic and gold nanoparticles. Epublished 2017, Anal Chim Acta. (May 2018) 1007:50-60.

(56)　　　　　　　References Cited

OTHER PUBLICATIONS

Oh et al., A three-line lateral flow assay strip for the measurement of C-reactive protein covering a broad physiological concentration range in human sera, Biosen Bioelectr., 2014, 61:285-289.

International Search Report and Written Opinion mailed Aug. 16, 2019 for Application No. PCT/US2019/035725.

Lelubre et al., Interpretation of C-reactive protein concentrations in critically ill patients, BioMed Res Int. 2013;2013(1):124021 in 11 pages.

Chikkaveeraiah et al., Microfluidic electrochemical immunoarray for ultrasensitive detection of two cancer biomarker proteins in serum. Biosens Bioelectr. Jul. 15, 2011; 26(11): 4477-4483.

Sakamoto et al., Magnetically promoted rapid immunoreactions using functionalized fluorescent magnetic beads: A proof of principle. Clin Chem.. Apr. 1, 2014; 60(4): 610-620.

Chen et al., "Dual gold nanoparticle lateflow immunoassay for sensitive detection of *Escherichia coli* O157:H7", Analytica Chimica Acta, vol. 876:71-76 (2015).

Seracare, Technical guide for Elisa, 2013; 44 pages.

SYSTEMS, DEVICES, AND METHODS FOR AMPLIFYING SIGNALS OF A LATERAL FLOW ASSAY

CROSS REFERENCE TO RELATED APPLICATIONS

This application is a continuation of PCT Application No. PCT/US2019/035725, filed Jun. 6, 2019, which claims the benefit of U.S. Provisional Application No. 62/686,606, filed Jun. 18, 2018, each of which is hereby incorporated by reference in its entirety.

FIELD

The present disclosure relates in general to lateral flow devices, test systems, and methods. More particularly, the present disclosure relates to lateral flow assay devices capable of measuring analyte present in a sample at low quantity or concentration by amplifying a detection signal.

BACKGROUND

Immunoassay systems, including lateral flow assays provide reliable, inexpensive, portable, rapid, and simple diagnostic tests. Lateral flow assays can quickly and accurately detect the presence or absence of, and in some cases quantify an analyte of interest in a sample. Advantageously, lateral flow assays can be minimally invasive and used as point-of-care testing systems.

Lateral flow assays generate a signal that can be measured to indicate the presence, absence, or quantity of an analyte of interest in a sample. When an analyte is present in a sample at low quantity or concentration, however, the signal generated by labeled analyte captured in a test region of the lateral flow assay may not exceed a detection threshold of a measurement system reading and processing the signal. As a result, a lateral flow assay may not provide a reliable or accurate indication that the analyte of interest is present in the sample.

SUMMARY

It is therefore an aspect of this disclosure to provide improved lateral flow assays that can detect the presence, absence, or quantity of an analyte in a sample. Embodiments of the methods and system described herein can measure the presence, and in some cases, the quantity or concentration, of an analyte even when the analyte is present at low quantity or concentration and would ordinarily result in a signal being generated at a level that is below a detection threshold of a measurement system. As a result, embodiments of the systems, devices, and methods described herein are very sensitive for analytes of interest even in low quantity or concentration. In addition, embodiments of the methods and system described herein can determine the absence of an analyte of interest in a sample with a higher degree of confidence than prior methods and systems. The absence of a detectable signal in embodiments of the present disclosure can reliably indicate the absence of the analyte of interest in the sample (as opposed to the analyte actually being present but at such a low concentration that the generated signal falls below the detection threshold of the system). Accordingly, embodiments of the present disclosure can decrease false negative readings. As will be described in detail below, lateral flow assays according to the present disclosure amplify a signal generated in a test region, such as a capture zone, of the lateral flow assay to a level that allows a conventional measurement system to detect an analyte of interest present in a sample at low quantity or concentration.

Signals generated by assays according to the present disclosure are described herein in the context of an optical signal generated by reflectance-type labels (such as but not limited to gold nanoparticle labels and different-colored latex particles). Although embodiments of the present disclosure are described herein by reference to an "optical" signal, it will be understood that assays described herein can use any appropriate material for a label in order to generate a signal, including but not limited to fluorescence-type latex bead labels that generate fluorescence signals and magnetic nanoparticle labels that generate signals indicating a change in magnetic fields associated with the assay.

Embodiments of the lateral flow assay described herein are particularly advantageous in diagnostic tests where an analyte of interest is present on the test strip at low quantity or low concentration. An analyte of interest may be present on the test strip at low concentration for many reasons, including but not limited to a limited quantity of analyte of interest present in a sample applied to the test strip and a limited volume of sample being applied to the test strip. Although embodiments of the present disclosure are described with reference to detecting an analyte of interest at low concentration, it will be understood that the present disclosure can also detect an analyte of interest in low quantities.

Some embodiments disclosed herein relate to a lateral flow assay for detecting an analyte of interest in a sample. The lateral flow assay includes a first conjugate comprising a first label, an agent configured to specifically bind to the analyte of interest, and a first binding partner; a second conjugate upstream of the first conjugate along a fluid flow path of the lateral flow assay, wherein the second conjugate comprises a second label and a second binding partner configured to specifically bind to the first binding partner; and a detection zone downstream of the first conjugate and the second conjugate along the fluid flow path of the lateral flow assay, the detection zone comprising an immobilized capture agent that specifically binds the analyte of interest.

The first conjugate can be present in a sample receiving zone of the lateral flow assay, or wherein the first conjugate is present in a first conjugate zone downstream of the sample receiving zone. The second conjugate can be present in a buffer receiving zone upstream of the sample receiving zone, or wherein the second conjugate is present in a second conjugate zone downstream of the buffer receiving zone and upstream of the sample receiving zone. The first conjugate can be configured to be solubilized and mobilize to the detection zone upon application of a fluid sample to the lateral flow assay. The second conjugate can be configured to be solubilized and mobilized to the detection zone after the first conjugate mobilizes to the detection zone.

The agent configured to specifically bind to an analyte of interest can be an antibody or antibody binding fragment that specifically binds the analyte of interest. The first binding partner and the second binding partner can include a binding pair selected from the group consisting of antigen/antibody, hapten/antibody, hormone/receptor, nucleic acid strand/complementary nucleic acid strand, substrate/enzyme, inhibitor/enzyme, carbohydrate/lectin, biotin/avidin, receptor/ligands, and virus/cellular receptor. The first binding partner and the second binding partner include a biotin/avidin binding pair, and the avidin can include streptavidin or neutravidin. The first binding partner and the second binding partner can include an antigen/antibody binding pair, and the antigen can include a peptide or a decapeptide. The analyte of interest can be a biological or environmental substance of interest. The analyte of interest can be an influenza virus. The influenza virus can be influenza A virus, influenza B virus, or influenza C virus. The immobilized capture agent can be an antibody or antibody binding fragment that specifically binds the analyte of interest. The test strip can include a nitrocellulose membrane. The lateral flow assay can also include a control zone comprising immobilized capture agent that specifically binds the first conjugate.

The first and second label can be selected from the group consisting of a metal nanoparticle, a blue latex bead, a metal nanoparticle, a colored latex particle, a colored latex bead, a magnetic particle, a carbon nanoparticle, a quantum dot, an up converting phosphor, an organic fluorophore, a textile dye, an enzyme, or a liposome. The first label and the second label can include a gold nanoparticle. The first label and the second label can be configured to generate an optical signal, a fluorescent signal, or a magnetic signal.

The lateral flow assay can also include a housing comprising a sample well positioned laterally above or upstream of the first conjugate, a buffer well positioned laterally above or upstream of the second conjugate zone, and a read window accessible to the detection zone. The buffer well, the second conjugate zone, the sample receiving well, and the first conjugate zone can be spatially separated along the fluid flow path of the lateral flow assay.

Further embodiments disclosed herein relate to a method of making the lateral flow assay. The method includes applying the first conjugate to a lateral flow test strip at or downstream of a sample receiving zone of the lateral flow test strip; and applying the second conjugate to the test strip at or downstream of a buffer receiving zone that is upstream of the sample receiving zone. The first conjugate and the second conjugate can be concurrently applied to the test strip. The first conjugate and the second conjugate can be applied to the test strip by air jet deposition.

Other embodiments described herein relate to a method of detecting an analyte of interest in a sample. The method includes applying a sample to a lateral flow assay. The lateral flow assay includes a first conjugate comprising a first label, an agent configured to specifically bind to the analyte of interest, and a first binding partner; a second conjugate upstream of the first conjugate along a fluid flow path of the lateral flow assay, wherein the second conjugate comprises a second label and a second binding partner configured to specifically bind to the first binding partner; and a detection zone downstream of the first conjugate and the second conjugate along the fluid flow path of the lateral flow assay, the detection zone comprising an immobilized capture agent that specifically binds the analyte of interest. The method also includes binding a complex to the immobilized capture agent in the detection zone, wherein the complex comprises analyte of interest bound to the first conjugate. After binding the complex, the method includes releasing the second conjugate to flow along the fluid flow path of the lateral flow assay. The method further includes binding the second conjugate to the complex bound in the detection zone.

The method can include detecting a signal generated by the complex and the second conjugate bound in the detection zone. The method can also include binding first conjugate that has not bound to the analyte of interest to the second conjugate bound to the complex in the detection zone. The first label and the second label can be configured to generate an optical signal, a fluorescent signal, or a magnetic signal.

The second conjugate can be released 5 seconds, 10 seconds, 15 seconds, 20 seconds, 25 second, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, or 10 minutes after applying a sample to the lateral flow device.

Binding the complex to the immobilized capture agent in the detection zone can include labeling the analyte of interest with the first conjugate to form a complex; and binding the complex to the immobilized capture agent in the detection zone. Releasing the second conjugate can include applying a buffer solution to the second conjugate or to a position on the lateral flow assay upstream of the second conjugate. Applying a buffer solution can include pouring a buffer solution in a buffer receiving well positioned laterally above or upstream of the second conjugate.

DETAILED DESCRIPTION

Figure 1:
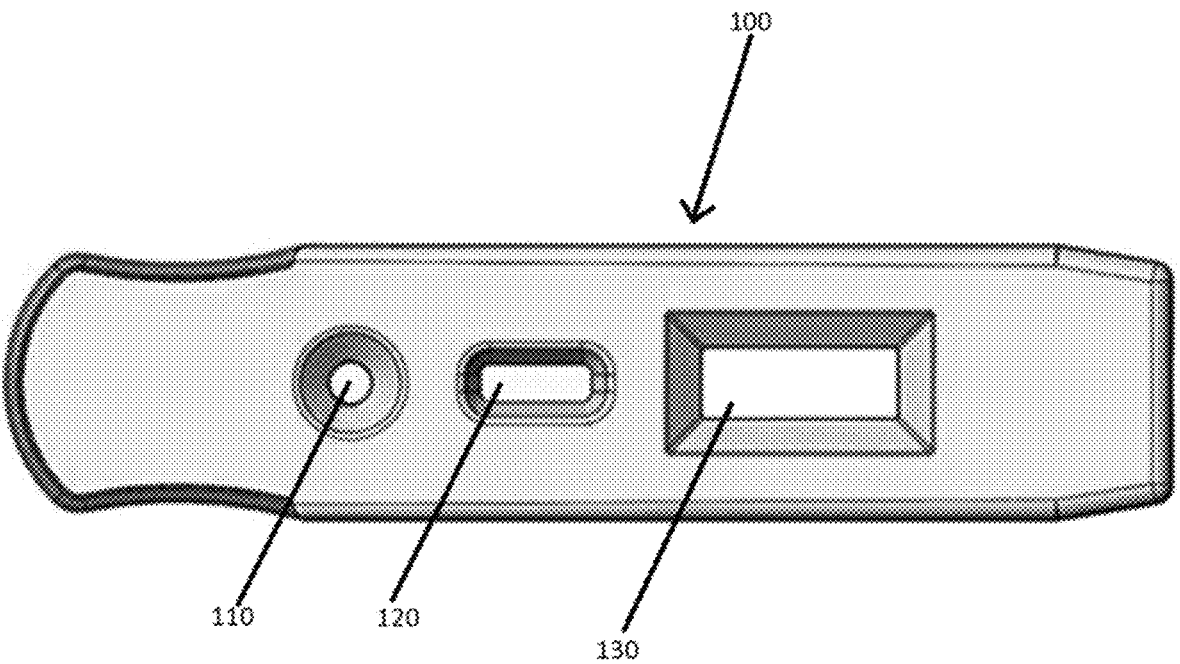
FIG. 1 illustrates a top view of an example lateral flow device according to the present disclosure including a buffer well, a sample well, and a read window.

Conventional lateral flow sandwich assays include a test strip having a conjugate pad (or labeling zone), a capture or test zone, and an absorbent pad arranged along a fluid flow path, which is typically but not necessarily arranged along a longitudinal axis of the test strip. The test strip may include a sample receiving zone or well upstream of the conjugate pad. The conjugate pad includes a labeled analyte-specific antibody, typically referred to as a conjugate. The label in this conjugate can include analyte-specific antibody conjugated to a detector molecule, such as but not limited to a gold nanoparticle. The capture zone includes immobilized capture agents, for example analyte-specific antibody immobilized on a carrier material, such as a nitrocellulose membrane. The absorbent pad assists a liquid sample applied to the conjugate pad (or to a sample receiving zone if present) to flow through the carrier material to the capture zone. When a liquid sample is applied to the test strip (at a sample receiving well or conjugate pad), the labeled analyte-specific antibody is rehydrated and becomes mobilizable. When antibody-specific analyte of interest is present, the analyte will bind to the labeled analyte-specific antibody and form an analyte-antibody-detector complex that moves downstream through the carrier material to the test zone. In the test zone, the analyte in the analyte-antibody-detector complex interacts with the analyte-specific antibody immobilized in the capture zone to form an antibody-analyte-antibody-detector structure, typically referred to as a sandwich. When a threshold number of these sandwich structures is formed in the capture zone, a signal generated by the detector molecules in the sandwich structures can be detected by a measurement system.

The measurement system can process the detected signal to determine the presence and in some cases the quantity of analyte of interest in the sample. If no analyte of interest is present in the sample, no analyte-antibody-detector complexes are formed, and as a result, no sandwich structures are formed in the capture zone. In this instance, there are no detector molecules in the capture zone and the measurement system correlates an absence of a signal from the capture zone with absence of analyte of interest in the sample. In cases where the analyte of interest is in fact present in the sample, but in very low quantity or concentration, the number of sandwich structures formed in the capture zone can be very low. In some instances, the number of sandwich structures is so low that the signal generated by detector molecules is below a detection threshold of the measurement system. In this case, the measurement system correlates an absence of a signal from the capture zone (or absence of a signal above a detection threshold of the system) with absence of analyte of interest in the sample, even though analyte of interest is in fact present in the sample but at a very low quantity or concentration. Accordingly, conventional lateral flow sandwich assays have limited sensitivity to analytes of interest that are present at low quantity or low concentration.

Devices, systems, and methods described herein solve these and other drawbacks by amplifying a signal that is generated in the presence of an analyte of interest in a sample applied to the lateral flow assay. Advantageously, embodiments of the devices, systems, and methods according to the present disclosure can amplify the signal generated at a test region, such as a capture zone, of the lateral flow assay to a level above a detection threshold of a conventional reader, even when the analyte of interest is present at low concentration. Lateral flow devices, test systems, and methods according to the present disclosure include a signal-amplification conjugate that binds to both (1) a first analyte-specific conjugate bound to immobilized capture agent in the capture zone, and (2) a second, residual analyte-specific conjugate that is present in the capture zone but not bound to immobilized capture agent. The second, previously unbound residual analyte-specific conjugate (that has become bound to a first signal-amplification conjugate in the capture zone) includes additional binding sites that interact and bind with a second signal-amplification conjugate, which itself interacts and binds with a third, residual analyte-specific conjugate present in the capture zone, and so on in a multi-level chain reaction of binding events in the capture zone.

The presence of additional analyte-specific conjugate that has become bound in the capture zone, made possible by binding interactions with the signal-amplification conjugate, can increase the intensity of the signal generated at the capture zone to a level that exceeds a detection threshold of a conventional measurement system. The presence of the signal-amplification conjugate bound in the capture zone can also increase the intensity of the signal generated at the capture zone to a level that exceed a detection threshold of the measurement system. Embodiments of the present disclosure improve sensitivity of a lateral flow assay by increasing the signal generated by the lateral flow assay into a conventionally-detectable range rather than modifying features of the measurement system, which advantageously allows the lateral flow assay according to the present disclosure to be backwards compatible with conventional lateral flow assay test systems.

Without being bound to any theory, it is believed that the signal-amplification conjugate forms a scaffold upon which additional analyte-specific conjugate that would ordinarily pass through the capture zone can be captured and retained in the capture zone, resulting in an amplified signal being generated at the capture zone. In addition to the detector molecule in the analyte-specific conjugate, the signal-amplification conjugate can also include a detector molecule, such that signal-amplification conjugate that becomes bound in the capture zone also generates a signal in the capture zone, thereby contributing to an increase in the intensity of the signal generated at the capture zone to a level above a detection threshold. Advantageously, embodiments of the present disclosure do not rely on or require that all or substantially all of the analyte of interest present in the sample bind to both analyte-specific conjugate and to immobilized capture agent in the capture zone in order for the signal in the capture zone to become amplified. It is an advantage of the present disclosure that even a very low level of analyte of interest (for example in the case of a sample having the analyte of interest present at a low concentration) binding to analyte-specific conjugate and capture agent immobilized in the capture zone allows a chain reaction of binding events to occur in the capture zone, independent of the presence or absence of analyte of interest within the scaffold that is formed after some amount, in some cases a very small amount, of analyte of interest binds with immobilized capture agent in the capture zone. Accordingly, embodiments of the system, devices, and methods described herein can greatly enhance sensitivity of a lateral flow assay for an analyte of interest that is present in a sample in even minute quantities.

In addition to increasing the sensitivity of lateral flow assays for measuring the presence, absence, or quantity of an analyte of interest in a sample at low concentrations, devices, systems, and methods described herein can advantageously be performed in a point of care setting without the use of highly-specialized, in some cases time-consuming, sample preparation techniques and detection systems that are typically used to analyze analytes in a sample at low concentrations, such as polymerase chain reaction (PCR). Embodiments of lateral flow devices described herein offer a convenient, easy-to-use format for users, rapidly generate signals that can be detected by a conventional reader, and can be performed in a point-of-care setting rather than an off-site laboratory facility.

The description is intended to be illustrative of a test strip for measuring analyte of interest in a test sample, even when present at low concentration. One of skill in the art will recognize that the example is intended to be exemplary, and that various modifications and variations may be employed on the lateral flow assays described herein. For example, a sample may include one or more analytes of interest present at low concentration, and the assay test strip may measure the one or more analytes of interest. In each of the various iterations, the lateral flow assay includes features according to the present disclosure to amplify a signal at the detection zone for measuring analyte in a test sample.

When more than a single analyte of interest is to be detected, for example, multiple analytes of interest in the sample, the detection zone may include a separate capture zone specific for each analyte of interest. For example, a sample may include three analytes of interest: a first analyte of interest, a second analyte of interest, and a third analyte of interest. The detection zone of the lateral flow assay would thus include three capture zones: a first capture zone specific to the first analyte of interest, a second capture zone specific to the second analyte of interest, and a third capture zone specific to the third analyte of interest.

Accordingly, the present disclosure provides assay test strips for measuring analyte of interest in a test sample, even when present at low concentration; lateral flow assays including the test strips; methods of measuring analyte of interest using the test strips described herein; and methods of making the assay test strips described herein.

Embodiments of the lateral flow assay described herein are particularly advantageous in diagnostic tests where a low quantity of analyte of interest is present on the test strip. Although embodiments of the present disclosure are described herein with reference to a low quantity of analyte being present on the test strip due to the analyte being present in a sample at low concentration, it will be understood that embodiments of the present disclosure are also applicable when a sample contains an amount of analyte that is capable of yielding a signal above a detection threshold but only a limited quantity of the sample is applied to the test strip.

Various aspects of the devices, test systems, and methods are described more fully hereinafter with reference to the accompanying drawings. The disclosure may, however, be embodied in many different forms. Based on the teachings herein one skilled in the art should appreciate that the scope of the disclosure is intended to cover any aspect of the devices, test systems, and methods disclosed herein, whether implemented independently of or combined with any other aspect of the present disclosure. For example, a device may be implemented or a method may be practiced using any number of the aspects set forth herein.

Although particular aspects are described herein, many variations and permutations of these aspects fall within the scope of the disclosure. Although some benefits and advantages are mentioned, the scope of the disclosure is not intended to be limited to particular benefits, uses, or objectives. Rather, aspects of the disclosure are intended to be broadly applicable to different detection technologies and device configurations some of which are illustrated by way of example in the figures and in the following description.

Conventional Lateral Flow Devices

Lateral flow devices described herein are analytical devices used in lateral flow chromatography. Lateral flow assays are assays that can be performed on lateral flow devices described herein. Lateral flow devices may be implemented on an assay test strip but other forms may be suitable, for example a dipstick, flow through device, or a microfluidic device. In the test strip format, a fluid sample, containing or suspected of containing an analyte, is placed on a sample receiving zone. Analyte of interest becomes labeled after it contacts the test strip. The now-labeled analyte of interest then flows (for example by capillary action) through the strip. The strip may be made of a medium such as paper, nitrocellulose, cellulose, fibers, or nylon or other material that allows flow of the sample through the medium.

Such assays are referred to as sandwich assays. Sandwich assays according to the present disclosure are described in the context of reflective-type labels (such as gold nanoparticle labels and different-colored latex particles) generating an optical signal, but it will be understood that assays according to the present disclosure may include latex bead labels configured to generate fluorescence signals, magnetic nanoparticle labels configured to generate magnetic signals, or any other label configured to generate a detectable signal. Sandwich-type lateral flow assays include a labeled conjugate deposited at a sample receiving zone on a solid substrate. After sample is applied to the sample receiving zone, the labeled conjugate dissolves or solubilizes in the sample, whereupon the labeled conjugate recognizes and specifically binds a first epitope on the analyte in the sample, forming a label-conjugate-analyte complex. This complex flows along the liquid front from the sample receiving zone through the solid substrate to a detection zone (sometimes referred to as a "test line" or "capture zone"), where immobilized capture agent (for example immobilized analyte-specific antibody) is located. In some cases where the analyte is a multimer or contains multiple identical epitopes on the same monomer, the labeled conjugate deposited at the sample receiving zone can be the same as the capture agent immobilized in the detection zone. The immobilized capture agent recognizes and specifically binds an epitope on the analyte, thereby capturing label-conjugate-analyte complex at the detection zone. The presence of labeled conjugate at the detection zone provides a detectable signal at the detection zone, if analyte is present in sufficient quantities. In one non-limiting example, gold nanoparticles are used to label the conjugate because they are relatively inexpensive, stable, and provide easily observable color indications due to the surface plasmon resonance properties of gold nanoparticles.

Detection of a signal generated at the detection zone can indicate that the analyte of interest is present in the sample. For example, if the signal exceeds a detection threshold of a measurement system, the measurement system can detect the presence and in some cases quantity of the analyte in the sample. However, absence of any detectable signal at the detection zone can indicate that the analyte of interest is not present in the sample or that it may be present below the detection limit. For example, if the sample did not contain any analyte of interest, the sample would still solubilize the labeled conjugate and the labeled conjugate would still flow to the detection zone. The labeled conjugate would not bind to the immobilized conjugate at the detection zone, however. It would instead flow through the detection zone, through a control line (if present), and, in some cases, to an optional absorbing zone. Some labeled conjugate would bind to the control agent deposited on the control line and generate a detectable signal at the control line, indicating that the device works properly. In circumstances where analyte is present but in an amount below the detection limit, label-conjugate-analyte complex binds at the detection zone, but is not detected. In these circumstances, the absence of a detectable signal emanating from the detection zone means that the user cannot definitively confirm whether analyte is absent from the sample or present in the sample below the detection limit of the measurement system.

Example Lateral Flow Signal-Amplification Devices According to the Present Disclosure Lateral flow assays, test systems, and methods described herein address these and other drawbacks of lateral flow assays that are not capable of ascertaining the difference between absence of analyte in a sample and presence of analyte in an amount below the detection limit. In addition to improving qualitative measurement of analytes, embodiments of the assays, test systems, and methods of the present disclosure can also greatly increase the sensitivity of measurements by a conventional reader, in some cases allowing quantitative measurement of analytes.

FIG. 1 illustrates an example lateral flow device 100 according to the present disclosure. An assay test strip is received within a housing of the device 100. In this non-limiting example of the lateral flow device 100, the housing defines a buffer well 110, a sample well 120, and a read window 130. The lateral flow device 100 may be of a size and shape for ease of use, rapid delivery of test results, portability, proper functioning and placement within an automated reader, economy in material use and cost, or other considerations. The size and shape is therefore not limited to any particular size or shape, and may be readily modified to fit the specific needs or requirements of the specific circumstances of use.

Figure 2:
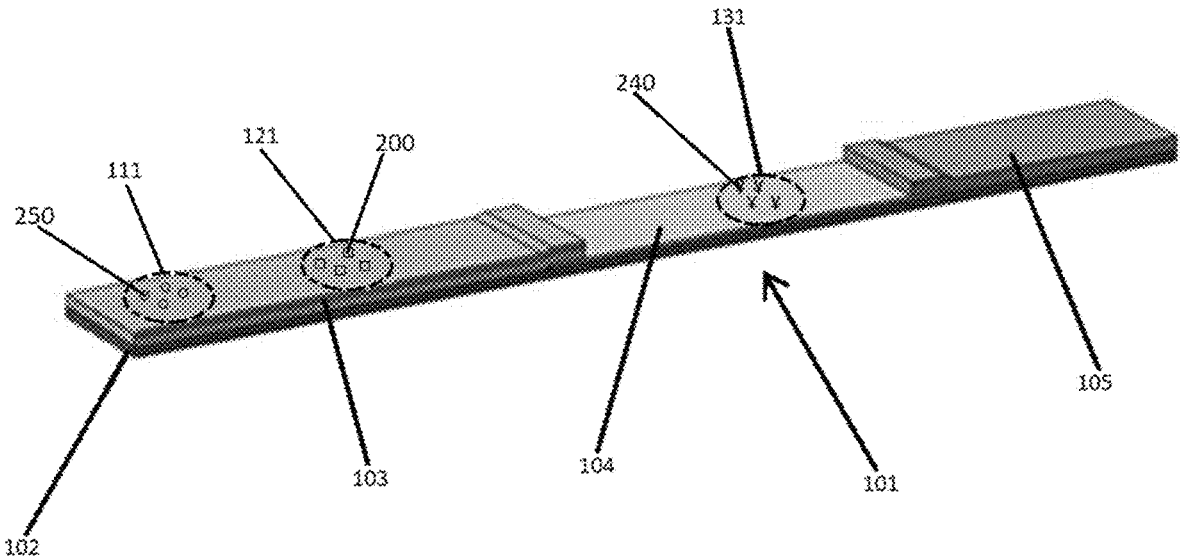
FIG. 2 illustrates an example assay test strip of a lateral flow signal-amplification assay according to the present disclosure.

FIG. 2 illustrates an example assay test strip 101 according to the present disclosure. The assay test strip 101 may be received or housed within the lateral flow device 100 of FIG. 1. The example assay test strip 101 in this non-limiting embodiment includes a substrate, an assay membrane having a sample receiving zone and a buffer receiving zone, a detection zone, and an absorbent pad. It will be understood that the present disclosure is not limited to this example assay test strip, and other assay test strips with different features can be implemented in accordance with the present disclosure.

In the embodiment of FIG. 2, the assay test strip 101 includes a backing card 102, a conjugate pad 103 having a sample receiving zone 121 and a buffer receiving zone 111, a membrane 104 having a detection zone 131, and an absorbent pad 105. The membrane 104 may be a nitrocellulose material. The assay test strip 101 is housed within the lateral flow device 100, such that the buffer receiving zone 111 is accessible through the buffer well 110, the sample receiving zone 121 is accessible through the sample well 120, and the detection zone 131 is accessible through the read window 130. Results of the assay may be measured at the read window 130 by measuring signals, if any, generated at the detection zone 131.

The backing card 102 may be any suitable material sufficient to support an assay test strip, for example, a water impervious layer, such as solid plastics, laminated sheets, composite materials, or the like. The absorbent pad 105 assists in promoting capillary action and fluid flow through the membrane, and may include any suitable material for absorbing fluid, including, for example, nitrocellulose, cellulosic materials, porous polyethylene pads, glass fiber filter paper, and so forth. The absorbent material may be treated with a surfactant to assist the wicking process.

Fluid is configured to flow along a longitudinal axis of the assay test strip 101 from the conjugate pad 103 to the absorbent pad 105. Components of the assay test strip 101 will be described with reference to this direction of fluid flow. For example, the membrane 104 is downstream of the conjugate pad 103 and upstream of the absorbent pad 105. For another example, the sample receiving zone 121 is downstream of the buffer receiving zone 111 and upstream of the detection zone 131.

The detection zone 131 of the membrane 104 includes immobilized capture agent configured to specifically bind an analyte of interest when present in the sample. The membrane 104 may further include additional detection zones for detecting more than one analyte of interest, and may include one or more control zones. The membrane 104 can be transparent in the visible region to minimize undesirable read interference for accurately determining the presence and/or quantity of an analyte of interest. Capture agent may be immobilized on or within the membrane 104 using any suitable method including, for example, depositing, spraying, soaking, immersing, pouring, or injecting capture agent on or within the membrane 104. For example, capture agent may be deposited and immobilized on the membrane 104 by preparing a solution including capture agent and spraying the solution onto the membrane 104 with air jet techniques. In another example, the capture agent is deposited by preparing a solution having capture agent and pouring the solution, spraying the solution, formulating the solution as a powder or gel that is placed or rubbed on the test strip, or any other suitable method.

The capture agent can be immobilized in any suitable amount in the detection zone 131 of the assay test strip 101. Advantageously, embodiments of the present disclosure can detect the presence, absence, and quantity of analyte of interest at low concentration using capture agent of a type and in an amount that is typical of conventional lateral flow sandwich assays. In some embodiments, the immobilized capture agent is present in an amount ranging from about 0.1-20 μL/test strip.

The conjugate pad 103 is placed over a portion of the backing card 102 in this example implementation. When the assay test strip 101 is housed within the lateral flow device 100, the buffer receiving zone 111 is accessible through, and in this case located laterally below, the buffer well 110. The sample receiving zone 121 is accessible through, and in this case located laterally below, the sample well 120. In some cases, the conjugate pad 103 may be fastened to the backing card 102. The conjugate pad 103 may be any suitable material for allowing flow of a fluid through the material, such as fibers (including glass fibers), polyester, or other material that provides flow of fluid through the conjugate pad 103. In this example implementation, the conjugate pad 103 includes an analyte-specific conjugate 200 deposited at the sample receiving zone 121. Embodiments of the analyte-specific conjugate 200 can also be referred to as "a first conjugate" according to the present disclosure. The analyte-specific conjugate 200 is configured to solubilize when a fluid is received in the sample receiving zone 121. As will be described below with reference to FIG. 3, the analyte-specific conjugate 200 includes a first label 210 (such as a detector molecule), a first binding partner 230, and an agent 220 that specifically binds analyte of interest 221 (when present in the sample). Thus, the analyte-specific conjugate 200 is configured to specifically bind to an analyte of interest (if present) in the sample received in the sample receiving zone.

In one example, the analyte-specific conjugate 200 is placed on or within the sample receiving zone 121. In another example, the analyte-specific conjugate 200 is placed on or within a first conjugate zone located downstream of the sample receiving zone 121 such that sample (and any analyte of interest if present) added to the sample receiving zone 121 will flow through the first conjugate zone and interact with analyte-specific conjugate 200. The analyte-specific conjugate 200 can be placed on or within the assay test device 101 using any suitable method, including, for example, depositing, spraying, soaking, immersing, pouring, or injecting analyte-specific conjugate on or within the sample receiving zone 121. For example, analyte-specific conjugate may be deposited by preparing a solution having analyte-specific conjugate and spraying the solution with air jet techniques. In another example, the analyte-specific conjugate may be prepared in a solution and deposited by pouring the solution, spraying the solution, formulating the solution as a powder or gel that is placed or rubbed on the test strip, or any other suitable method.

The analyte-specific conjugate 200 can be provided in any suitable amount in the sample receiving zone 121 (or other suitable location) of the assay test strip 101. Advantageously, embodiments of the present disclosure can detect the presence, absence, and quantity of analyte of interest at low concentration using analyte-specific conjugate 200 of a type and in an amount that is typical of conventional lateral flow sandwich assays. In some embodiments, the analyte-specific conjugate is deposited in an amount ranging from about 0.1-20 μL/test strip.

Embodiments of systems, devices, and methods according to the present disclosure include a signal-amplification conjugate 250. Embodiments of the signal-amplification conjugate 250 can also be referred to as "a second conjugate" according to the present disclosure. As will be described below with reference to FIG. 3, signal-amplification conjugate 250 includes a second label 211 and a second binding partner 231. The second binding partner 231 is configured to specially bind the first binding partner 230 of the analyte-specific conjugate 200. The signal-amplification conjugate 250 is present on or added to a location upstream of the analyte-specific conjugate 200. In one example described with reference to FIG. 2, the signal-amplification conjugate 250 is added to the assay test strip 101 during a manufacturing process. In another example, the signal-amplification conjugate 250 is added to the assay test strip 101 by an operator during a test event. It will be understood that embodiments of the present disclosure are not limited by the manner in which the signal-amplification conjugate 250 is introduced into the lateral flow assay, and that other examples in addition to those described herein are suitable.

In one example illustrated in FIG. 2, the signal-amplification conjugate is placed on or within the buffer receiving zone 111. In another example, the signal-amplification conjugate 250 is placed on or within a second conjugate zone that is located downstream of the buffer receiving zone 111 and upstream of the sample receiving zone 121, such that sample (and any analyte of interest if present) added to the sample receiving zone 121 will not interact with signal-amplification conjugate 250 in the second conjugate zone. This spatial orientation also ensures that buffer added to the buffer receiving zone 111 will flow downstream through the second conjugate zone and solubilize the signal-amplification conjugate 250. Although the non-limiting implementation of FIG. 2 does not rehydrate the signal-amplification conjugate 250 using the sample solution, it will be understood that other implementations are suitable. For example, another implementation of the present disclosure could use a single solution (such as a sample solution) to rehydrate both the analyte-specific conjugate 200 and the signal-amplification conjugate 250. In this case, the sample solution can be applied at different times to ensure that the signal-amplification conjugate 250 mobilizes down the fluid path to the detection zone of the test strip after the analyte-specific conjugate 200 has mobilized down the fluid path to the detection zone.

The signal-amplification conjugate 250 can be placed on or within the assay test device using any suitable method, including, for example, depositing, spraying, soaking, immersing, pouring, or injecting signal-amplification conjugate 250 on or within the buffer receiving zone 111 (or other suitable location). For example, signal-amplification conjugate 250 may be deposited by preparing a solution having signal-amplification conjugate 250 and spraying the solution with air jet techniques. In another example, the signal-amplification conjugate 250 may be prepared in a solution and deposited by pouring the solution, spraying the solution, formulating the solution as a powder or gel that is placed or rubbed on the test strip, or any other suitable method.

It will be understood that the signal-amplification conjugate 250 can be added to the assay test strip in areas other than the buffer receiving zone 111. For example, in one non-limiting embodiment, the lateral flow device 100 does not include a separate or dedicated location, such as a buffer well or a buffer receiving zone, to receive the signal-amplification conjugate 250 onto the assay test strip 101. The signal-amplification conjugate 250 can be added to the assay test strip 101 in any suitable location after the analyte-specific conjugate 200 has solubilized in the sample receiving zone 121 and mobilized to the detection zone 131.

Embodiments of the signal-amplification conjugate 250 of the present disclosure can be provided in any suitable amount in the buffer receiving zone 111 (or other suitable location) of the assay test strip 101. In some embodiments, the signal-amplification conjugate 250 is deposited in an amount ranging from about 0.1-20 μL/test strip. In some embodiments, the signal-amplification conjugate 250 is deposited in an amount of 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 16, 17, 18, 19, or 20 μL/test strip on the assay test strip 101.

The signal-amplification conjugate 250 is placed on or added to the assay test strip 101 upstream of the location where analyte-specific conjugate 200 is placed on or added to the assay test strip 101. The signal-amplification conjugate 250 and the analyte-specific conjugate 200 may be placed on the test strip at the same time or at different times, during a process of making the assay test strip 101 or by an operator performing a test event using the assay test strip 101. In one non-limiting example, both the signal-amplification conjugate 250 and the analyte-specific conjugate 200 are added to the assay test strip 101 at the same time or substantially the same time but at different locations of the assay test strip 101, for example, by introducing or depositing both signal-amplification and analyte-specific conjugate on the test strip simultaneously or nearly simultaneously. In this example, the analyte-specific conjugate 200 is added to or positioned on the assay test strip 101 downstream of the location where the signal-amplification conjugate 250 is added or positioned. This spatial orientation minimizes interaction between the conjugates prior to the analyte-specific conjugate mobilizing to and becoming bound at the detection zone 131. In another non-limiting example, the signal-amplification conjugate 250 is added to the assay test strip 101 before or after addition of the analyte-specific conjugate 200 at any suitable location and using any suitable method or technique, including but not limited to those described herein. For example, the signal-amplification conjugate 250 may be added to the same or substantially the same location that the analyte-specific conjugate 200 was initially added, if the signal-amplification conjugate 250 is added after the analyte-specific conjugate 200 has mobilized to and become bound in the detection zone 131.

In some embodiments, the lateral flow device 100 does not include a separate or dedicated location, such as a buffer well or a buffer receiving zone, that includes the signal-amplification conjugate 250 prior to a test event using the assay test strip 101. Instead, the signal-amplification conjugate 250 is introduced to the assay test strip 101 by an operator during the test event. For example, the signal-amplification 250 conjugate can be introduced to the assay test strip after a sample is introduced to the assay test strip. Specifically, a sample is first placed in the sample receiving zone, and the sample is allowed to migrate through the test assay strip for a suitable period of time. The period of time can be a sufficient amount of time for the analyte-specific conjugate 200 to solubilize, form binding interactions with analyte of interest in the sample (if present), mobilize to the detection zone, and form binding interactions with immobilized capture agent in the detection zone. After incubation for a suitable period of time, a solution including signal-amplification conjugate 250 is introduced to the lateral flow device 100. The signal-amplification conjugate 250 then migrates through the assay test strip 101 to the detection zone 131.

The period of delay between adding the sample and the signal-amplification conjugate 250 to the assay test strip 101 can be adjusted based on various parameters, including but not limited to characteristics of the analyte of interest, the fluid containing or suspected of containing the analyte of interest, the analyte-specific conjugate 200, the signal-amplification conjugate 250, and material properties of the assay test strip 101. Example periods of delay include but are not limited to 5 seconds, 10 seconds, 15 seconds, 20 seconds, 25 second, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 12 minutes, and 15 minutes. Thus, in this example, signal-amplification conjugate 250 is not present on the assay test strip 101 at the start of a test event. Accordingly, it will be understood that embodiments of the present disclosure for amplifying the signal of an analyte present in low concentration, such as at a concentration below a detection limit, can be achieved using n signal-amplification conjugate 250 in a variety of ways, including preparing the test strip with the signal-amplification conjugate 250 present or adding the signal-amplification conjugate 250 at a later step.

Embodiments of the systems, devices, and methods according to the present disclosure can detect an analyte of interest very rapidly. The total time from the beginning of a test event (defined as the time when a sample is added to the test strip) to the end of the test event (defined as the time when a measurement system detects signals generated at the detection zone, if any) can be but is not limited to 1 minute, 2 minutes, 3 minutes, 4 minutes, 5 minutes, 6 minutes, 7 minutes, 8 minutes, 9 minutes, 10 minutes, 12 minutes, and 15 minutes.

Figure 3:
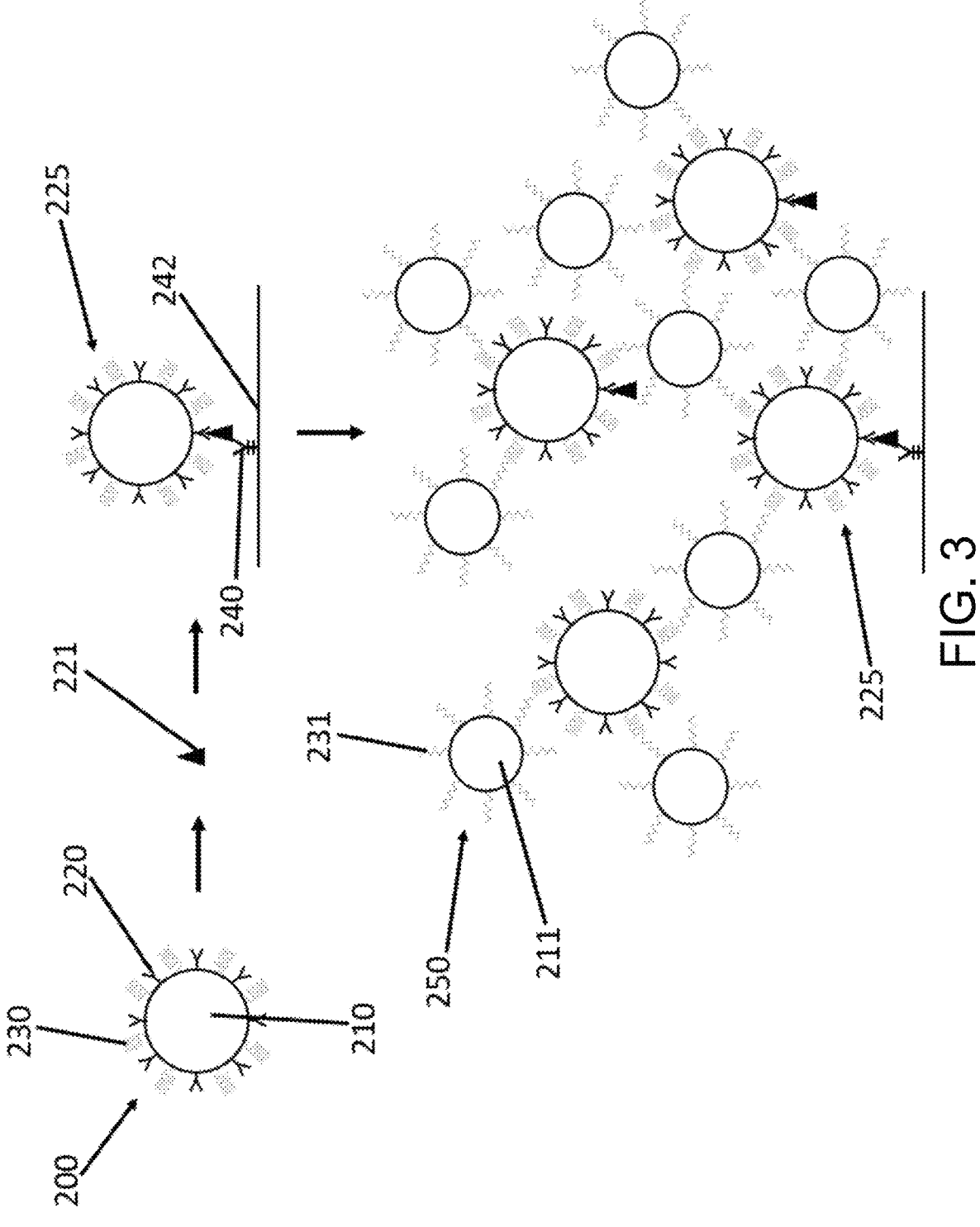
FIG. 3 schematically illustrates an example method of amplifying a signal generated by an assay test strip according to the present disclosure.

FIG. 3 schematically illustrates an example embodiment of the systems, devices, and methods according to the present disclosure. Without being bound to any particular theory, a process by which analyte-specific conjugate 200 binds with analyte of interest 221, a capture agent 240 immobilized in a capture zone 242, and a signal-amplification conjugate 250 will now be described with reference to FIG. 3, but it will be understood that the present disclosure is not limited to the schematic diagram of FIG. 3.

The analyte-specific conjugate 200 includes a first label 210, a first binding partner 230, and an agent 220 that specifically binds analyte of interest 221 (when present in the sample). The agent 220 is configured to specifically bind analyte of interest 221, and may include an antibody or binding fragment of an antibody that specifically binds the analyte of interest 221. The analyte-specific conjugate 200 is deposited on or added to the sample receiving zone 121 (or any other suitable location) of the assay test strip 101 using, for example, methods described above with reference to FIG. 2. A sample is added to the assay test strip 101, for example at the sample receiving zone 121. Analyte-specific conjugate 200 solubilizes into the sample, and agent 220 specifically binds to analyte of interest 221 when present in the sample, forming an analyte-agent-first label complex 225. The complex 225 flows through the assay test strip 101 to the detection zone 131, which includes immobilized capture agent 240 that is configured to specifically bind analyte of interest 221. The complex 225 is captured at the detection zone 131, as shown in FIG. 3.

After a suitable period of time has passed to allow complex 225 to travel to and become captured in the detection zone 131, a signal-amplification conjugate 250 according to the present disclosure is caused to travel downstream along the assay test strip 101 to the detection zone 131. Signal-amplification conjugate 250 includes a second label 211 and a second binding partner 231. In one non-limiting implementation, the signal-amplification conjugate 250 is present on the assay test strip 101 before the sample is added (having been deposited in any suitable manner including those described above with reference to FIG. 2), and is caused to travel downstream to the detection zone 131 by applying a buffer solution to the signal-amplification conjugate 250. In this implementation, the previously deposited signal-amplification conjugate 250 is deposited upstream of the sample receiving zone 121, for example in a buffer receiving zone 111 located upstream of the sample receiving zone 121. This spatial orientation of the signal-amplification conjugate 250 in a buffer receiving zone 111 upstream of the analyte-specific conjugate 200 in a sample receiving zone 121 ensures that addition of the sample to the sample receiving zone 121 will solubilize and mobilize the analyte-specific conjugate 200 and not the signal-amplification conjugate 250. In another non-limiting implementation, the signal-amplification conjugate 250 is added to the assay test strip 101 after a suitable period of time has elapsed following addition of the sample to the sample receiving zone. In this implementation, a buffer solution including the signal-amplification conjugate 250 can be added to the assay test strip 101 at a buffer receiving zone 111 (if present), at the sample receiving zone 121, or any other suitable location of the assay test strip 101.

In both of these implementations, embodiments of the present disclosure allow the analyte-specific conjugate 200 to mobilize and bind to capture agent 240 in the detection zone 131 before being exposed to, and forming binding interactions with, signal-amplification conjugate 250. Embodiments of the present disclosure advantageously allow the timing of release of the signal-amplification conjugate 250 to be tailored to the specific characteristics of the lateral flow assay, and to be triggered only when buffer solution is added to the system (either to a buffer receiving zone 111 containing signal-amplification conjugate 250, or to any suitable location when the buffer solution itself contains signal-amplification conjugate 250). These embodiments of the present disclosure also advantageously prevent interactions between the analyte-specific conjugate 200 and the signal-amplification conjugate 250 from occurring in locations of the assay test strip 101 where they are not desirable, namely locations upstream of the detection zone 131. Thus, embodiments of the present disclosure that allow the timing of release of the signal-amplification conjugate 250 to an optimal time (after a sufficient quantity of analyte-specific conjugate 200 has mobilized to and become bound in the detection zone 131) advantageously maximize the occurrence of binding interactions between the analyte-specific conjugate 200 present in the detection zone (whether bound or unbound to capture agent 240) and signal-amplification conjugate 250 in the optimal location—the detection zone 131. This results in an aggregation and increase in the signal generated by the conjugates 200, 250 in the detection zone to a level above a detection threshold.

After buffer solution is added to the assay test strip 101 and either introduces signal-amplification conjugate 250 directly into the system or solubilizes signal-amplification conjugate 250 already present in the system, a second series of binding events will occur due to the properties of the signal-amplification conjugate 250 of the present disclosure. As described above, the second binding partner 231 specifically binds to the first binding partner 230 of the analyte-specific conjugate 200. Without being bound to any particular theory, it is believed that when the signal-amplification conjugate 250 flows through the assay test strip 101 to the detection zone 131, the second binding partner 231 of the signal-amplification conjugate 250 specifically binds to the first binding partner 230 of the complex 225 bound to capture agent 240, whereby the signal-amplification conjugate 250 is captured at the detection zone 131. The second label 211 of the now-bound signal-amplification conjugate 250 generates a signal in the detection zone. In this way, the signal from a single analyte-specific conjugate 200 bound at the detection zone is amplified. In some embodiments, a single analyte-specific conjugate 200 in a complex 225 binds to a plurality of signal-amplification conjugates 250, which themselves contribute to the signal generated by the single analyte-specific conjugate 200 in the complex 225. In some embodiments of the present disclosure, even this first-level binding interaction between the complex 225 and one or more signal-amplification conjugates 250 can be sufficient to increase the signal generated in the detection zone above a threshold detection level.

Advantageously, embodiments of the present disclosure can produce an even higher level of signal amplification than that made possible by the first-level binding interaction alone. In embodiments of systems, devices, and methods described herein, amplification of the signal generated at the detection zone is further enhanced by the ability of the now-bound signal-amplification conjugates 250 to bind with residual analyte-specific conjugate 200 that is present in the detection zone but did not bind to capture agent 240. This residual analyte-specific conjugate 200 might ordinarily pass through the detection zone 131 or remain diffusely scattered in the detection zone in a conventional lateral flow assay. In the presence of signal-amplification conjugate 250 according to the present disclosure, this residual analyte-specific conjugate 200 can become bound in a scaffold of conjugate that is anchored to the detection zone 131 via complex 225, and further contribute to the aggregate signal generated at the detection zone 131. Signals generated by embodiments of the present disclosure can increase in intensity in an exponential manner. Thus, in some embodiments, the signal intensity generated at the detection zone 131 can increase due to the amplification of the signal by an amount of 2-100 fold, for example, by an amount of 2, 3, 4, 5, 6, 7, 8, 9, 10, 15, 20, 25, 30, 40, 50, 60, 70, 80, 90, or 100 fold. It will be understood that the present disclosure is not limited to these example levels of amplification, and that other levels of amplification are made possible with embodiments of the present disclosure.

Advantageously, the above-described chain reaction of binding events can occur in the presence of even very low quantity of analyte of interest in the sample. Without being bound to any particular theory, it is believed that residual analyte-specific conjugate 200 can form binding interactions with signal-amplification conjugate 250 independent of whether or not the residual analyte-specific conjugate 200 bound to analyte in the sample. In other words, the binding interactions occurring after the first interaction between complex 225 and signal-amplification conjugate 250 rely on this first interaction to ensure the chain reaction of binding events occur in a localized area (the detection zone), but they do not rely on additional analyte of interest to form the scaffold of bound conjugate 200, 250 pairs that amplifies the signal generated by the complex 225.

It is also an advantage of the present disclosure that the absence of a signal at the detection zone 131 can be correlated to an absence of analyte of interest in the sample with a high degree of confidence. In the absence of analyte of interest in the sample, complex 225 will not form and bind to capture agent 240 in the detection zone 131. In the absence of this binding event, the signal-amplification conjugate 250 will not become bound in the detection zone 131 and will pass through the detection zone 131 to the absorbent pad 151.

As used herein, a buffer refers to a solution used in lateral flow assays that does not interfere with binding interactions, does not denature analyte of interest or other components of the device, and that retains neutrality for the purpose of flowing components through a test strip. Various buffers are well known, and any of a variety of buffers may be used for the specific analytes, compounds, and components used in the lateral flow assays described herein. In some embodiments, the buffer is a phosphate buffered saline (PBS).

Embodiments of the present disclosure have been described with reference to a chase buffer being added to a buffer receiving zone located upstream of a sample receiving zone, and to a buffer solution including signal-amplification conjugate being added to any suitable location of the assay test strip after a sample has been added. It will be understood however, that other methods to add or release a buffer solution into the system will be suitable and can be used in embodiments of the present disclosure. For example, a chase buffer solution can be prepackaged in a sachet bag or other appropriate structure and incorporated on the assay test strip upstream of deposited signal-amplification conjugate and a sample receiving well of the assay test strip. The chase buffer solution can be released by breaking the sachet bag using any appropriate mechanism at a suitable time after the sample has been added to the assay test strip.

In some embodiments, the signal-amplification conjugate 250 does not bind to other conjugates (such as to the analyte-specific conjugate 200) until reaching the detection zone 131. In some embodiments, binding of signal-amplification conjugate 250 to other conjugates can result in precipitation of the bound conjugates, resulting in a smear of precipitated label through the test strip, thereby interfering with or confounding the results. As described above, embodiments of the present disclosure include features to prevent or minimize this precipitation of bound conjugates upstream of the detection zone 131. These features ensure that the signal-amplification conjugate 250 remains solubilized in solution, and does not bind with analyte-specific conjugate 200 before reaching the analyte-specific conjugate 200 in the complex 225 that has been captured in the detection zone 131. In one example, embodiments of the present disclosure include depositing signal-amplification conjugate 250 on the assay test strip 101 upstream of the analyte-specific conjugate 200 in the sample receiving zone 121, and solubilizing the signal-amplification conjugate 250 only after the analyte-specific conjugate has first had an opportunity to flow through the lateral flow device to the detection zone 131. In another example, embodiments of the present disclosure include adding signal-amplification conjugate 250 in a buffer solution that is applied to the assay test strip 101 only after the analyte-specific conjugate 200 has first had an opportunity to flow through the lateral flow device to the detection zone 131.

The first label 210 of the analyte-specific conjugate 200 can be the same label as the second label 211 of the signal-amplification conjugate 250. In one non-limiting example, the first label 210 and the second label 211 may be a colloidal gold label. The colloidal gold label may include a gold nanoparticle. The first label 210 and the second label 211 may include any suitable label that may provide a detectable signal. Thus, in some embodiments, the first label 210 and the second label 211 is an enzyme, colloidal metal particle (also referred to as metal nanoparticle, such as gold or silver nanoparticles), colored latex particle, radioactive isotope, co-factor, ligand, chemiluminescent or fluorescent agent, protein-adsorbed silver particle, protein-adsorbed iron particle, protein-adsorbed copper particle, protein-adsorbed selenium particle, protein-adsorbed sulfur particle, protein-adsorbed tellurium particle, protein-adsorbed carbon particle, or protein-coupled dye sac, or any other suitable label.

As described above, the agent 220 is an agent that specifically binds analyte of interest 221, and may include an antibody or binding fragment of an antibody that specifically binds the analyte of interest 221. Thus, the agent 220 can be an anti-analyte antibody. The first binding partner 230 of the analyte-specific conjugate 200 specifically binds to the second binding partner 231 of the signal-amplification conjugate 250, and thus the first and second binding partners 230, 231 constitute a binding pair. This binding pair may include, for example, a binding pair selected from the group consisting of antigen/antibody, hapten/antibody, hormone/receptor, nucleic acid strand/complementary nucleic acid strand, substrate/enzyme, inhibitor/enzyme, carbohydrate/lectin, biotin/avidin, receptor/ligands, or virus/cellular receptor. In one non-limiting example, the first binding partner 230 is avidin (or a derivative or analogue thereof) and the second binding partner 231 is biotin (or a derivative or analogue thereof). For example, the analyte-specific conjugate 200 can be biotinylated and the signal-amplification conjugate 250 can include an anti-biotin antibody or streptavidin binding partner. In another non-limiting example, the binding pair is antigen/antibody, such as a peptide and an antibody. In some embodiments, the peptide is a decapeptide. In a further non-limiting example, the binding pair is doxorubicin and anti-doxorubicin. In still a further non-limiting example, the binding pair is methotrexate and anti-methotrexate. In yet another non-limiting example, the binding pair is FITC and anti-FITC antibody. It will be understood that embodiments of the present disclosure can use any suitable first binding partner 230 that specifically binds a second binding partner 231 and are not limited to the above-examples.

It is an advantage of embodiments of the present disclosure that the second binding partner 231 of the signal-amplification conjugate 240 can be selected to bind specifically to the first binding partner 230 of the analyte-specific conjugate 200 without interfering with binding of the analyte of interest 221 with the analyte-specific antibody of the analyte-specific conjugate 200. In one example, a different protein/peptide can be co-conjugated with an analyte-specific antibody onto the first label 210 to form the analyte-specific conjugate 200. In another example, another protein/peptide can be first biotinylated and then co-conjugated with the analyte-specific antibody onto the first label 210 to form the analyte-specific conjugate 200. In a further example, small molecules, such as biotin, are added to the analyte-specific antibody, which is later conjugated to the first label 210 of the analyte-specific conjugate 200, and the signal-amplification conjugate 250 includes the small molecule specific binding protein/antibody. In this example, the small molecules added to the analyte-specific antibody are selected so that they do not interfere with the binding of analyte to the analyte-specific antibody in the analyte-specific conjugate 200. In still another example, rather than biotin, the protein/peptide can be conjugated to another molecular against which another antibody or binding protein exists. The added protein/peptide, biotin, or other molecules that are conjugated to the first label 210 can thus provide binding sites for an antibody against this protein/peptide, biotin, or other molecular on the signal-amplification conjugate 250, without interfering with the analyte-specific binding interaction between the analyte of interest 221 and the analyte-specific antibody conjugated to the first label 210.

In some embodiments, the lateral flow device includes one or more control zones. The control zones may be in the detection zone or separate from the detection zone. In some embodiments, a control zone may be a positive control zone, which may include small molecules conjugated with a protein, such as bovine serum albumin (BSA). Positive control labeled antibody that specifically binds small molecules may be deposited on the conjugate pad. When positive control labeled antibody is rehydrated with a liquid sample it flows towards the positive control zone and binds to the small molecules forming a semi-sandwich. In some embodiments, a positive control zone includes immobilized capture agents that specifically bind to analyte-specific conjugate, such that analyte-specific conjugate that does not bind to analyte of interest passes through a detection zone (a test line) and specifically binds to immobilized capture agents at the control line, generating a signal that indicates proper functioning of the lateral flow device. It will be understood that any suitable control zone can be implemented in embodiments of the present disclosure.

Embodiments of readers and data analyzers disclosed herein can process the signal measurements obtained from the control zone to correct the signal measured at the detection zone or to alert an operator that the test was invalid.

As used herein, "analyte" generally refers to a substance to be detected. In some embodiments, analytes are those that are sometimes found in a sample in low concentration, such as at concentrations below a detection limit of a measurement system. Some analytes are typically present in a sample at high concentrations, but may be present in a particular sample to be tested at low concentration due to a particular disorder, due to the phase of a disorder, or due to sample processing. For example, an analyte may be present in a sample at low concentration at initial stages of a disease or disorder or following a peak stage of a disease or disorder. It will be understood that embodiments of the present disclosure are applicable to lateral flow assays measuring any analyte that is present or suspected to be present in a sample in low quantities or where the sensitivity of measuring such analytes is low.

Analytes may include antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles, and metabolites of or antibodies to any of the above substances. In some embodiments, the analyte of interest is an influenza virus, such as an influenza A, influenza B, or influenza C virus. Additional analytes may be included for purposes of biological or environmental substances of interest.

In some embodiments, a sample may include one or more analytes of interest, and thus the lateral flow device may be configured for detecting one or more analytes of interest. In order to detect one or more analytes of interest, the lateral flow device according to the present disclosure can include one or more analyte-specific conjugates 200, wherein each analyte-specific conjugate 250 specifically binds to an analyte of interest. Thus, for example, a first analyte-specific conjugate 200A specifically binds to a first analyte of interest 221A, a second analyte-specific conjugate 200B specifically binds to a second analyte of interest 221B, a third analyte-specific conjugate 200C specifically binds to a third analyte of interest 221C, and so forth for a desired number of analytes of interest present or suspected of being present in the sample. In some embodiments, each analyte-specific conjugate that specifically binds to an analyte of interest does not specifically bind to any other analyte of interest. Furthermore, in some embodiments, each analyte-specific conjugate may have an identical label or a label that is different from each other analyte-specific conjugate. Thus, for example, each analyte-specific conjugate may include a unique label that is different from any other label of an analyte-specific conjugate. Furthermore, where one or more analyte of interest is present, the lateral flow device may include one or more capture lines, each capture line including immobilized capture agent that specifically binds one particular analyte of interest. For example, a first capture agent 240A immobilized in a capture zone 242A specifically binds a first analyte of interest 221A, a second capture agent 240B immobilized in a capture zone 242B specifically binds a second analyte of interest 221B, a third capture agent 242C immobilized in a capture zone 242C specifically binds a third analyte of interest 221C, and so on for a desired number of analytes of interest that are being analyzed in a test sample.

In some embodiments where the lateral flow device is configured for measuring one or more analytes of interest, the device further includes a signal-amplification conjugate 250. The signal-amplification conjugate 250 can includes one binding partner of a binding pair that specifically binds to another binding partner of the binding pair. In some embodiments, a signal-amplification conjugate binds to a first analyte-specific conjugate, a second analyte-specific conjugate, a third analyte-specific conjugate, and so forth for a desired number of analytes of interest, thereby amplifying the signal for each analyte of interest. In some embodiments, the signal-amplification conjugate binds to one, two, three, or more analyte-specific conjugates, thereby amplifying the signal only for a desired number of analytes, for example, only for the analytes of interest that are known to be or suspected of being present in a sample at low concentration.

It is to be understood that analytes of interest are often present in a sample at various concentrations, and thus, amplification of a signal may not be required for each analyte of interest, but only for those analytes of interest that are known to be or suspected of being present in low concentration, such as at a concentration below the detection limit of a measurement system. Accordingly, in some embodiments, a first analyte-specific conjugate that specifically binds a first analyte present at low concentration includes a binding partner, whereas a second analyte-specific conjugate that specifically binds a second analyte present at concentrations above a detection limit does not include a binding partner, whereby the signal-amplification conjugate will bind to the first analyte-specific conjugate but not the second analyte-specific conjugate, thereby amplifying the signal of the first analyte of interest. Various iterations of the present disclosure may be implemented, for example, by amplifying any desired signal, including a signal that is below a detection limit of a measurement system.

The following non-limiting examples illustrate features of lateral flow devices, test systems, and methods described herein, and are in no way intended to limit the scope of the present disclosure.

Example 1

Preparation of a Lateral Flow Assay According to the Present Disclosure

The following example describes preparation of a lateral flow assay according to the present disclosure to measure analyte present in a sample at low concentration. In this non-limiting example, the analyte of interest is influenza A ("Flu A").

A test strip was prepared having a conjugate pad with a sample receiving zone and a buffer receiving zone. An analyte-specific conjugate was prepared in solution and the solution was sprayed on the sample receiving zone by air jet deposition. Briefly, anti-Flu A antibody and biotin were incubated with gold nanoparticles to form analyte-specific conjugate. The analyte-specific conjugate was deposited in an amount of 7 µL/test strip onto a conjugate pad at the sample receiving zone by spraying a solution including the analyte-specific conjugate with air jet. The conjugate pad was heated to dry the analyte-specific conjugate to the conjugate pad. The amount of anti-Flu A antibody used to formulate the analyte-specific conjugate deposited on the conjugate pad was about 260 ng per test strip.

A signal-amplification conjugate was prepared in solution and the solution was sprayed on the buffer receiving zone by air jet deposition. Briefly, anti-biotin was incubated with gold nanoparticles to form signal-amplification conjugate. The signal-amplification conjugate was deposited in an amount of 2 µL/test strip onto a conjugate pad at the buffer receiving zone by spraying a solution including the signal-amplification conjugate with air jet. The conjugate pad was heated to dry the signal-amplification conjugate to the conjugate pad. The amount of anti-biotin antibody used to formulate the signal-amplification conjugate deposited on the conjugate pad was about 74 ng per test strip.

In addition, the test strip was prepared having a detection zone. The detection zone included an immobilized capture agent that specifically binds Flu A. In this example, anti-Flu A antibody was deposited at the detection zone in an amount of 2.4 mg/mL at 0.75 µL/cm.

In this example, the detection zone also included a positive control capture zone. The positive control capture zone was prepared to ensure that the assay functions properly. In this example, the positive control capture zone included immobilized bovine serum albumin derivatized with anti-biotin (BSA-anti-biotin). The immobilized BSA-biotin captured signal-amplification conjugate present on the test strip that rehydrated with the buffer and flowed to the positive control zone, indicating proper function of the assay. The signal-amplification conjugate was captured at the positive control line, and a positive control signal indicated proper function of the assay.

The test strip was placed into a lateral flow device having a housing to hold the test strip. The lateral flow device included a buffer well placed over the buffer receiving zone, a sample well placed over the sample receiving zone, and a read window placed over the detection zone, as shown in FIG. 1.

Example 2

Amplification of Signal of Analyte at Low Concentration

The following example demonstrates the use of the lateral flow assay described in Example 1 for detecting low concentration of Flu A in a sample.

Figure 4:
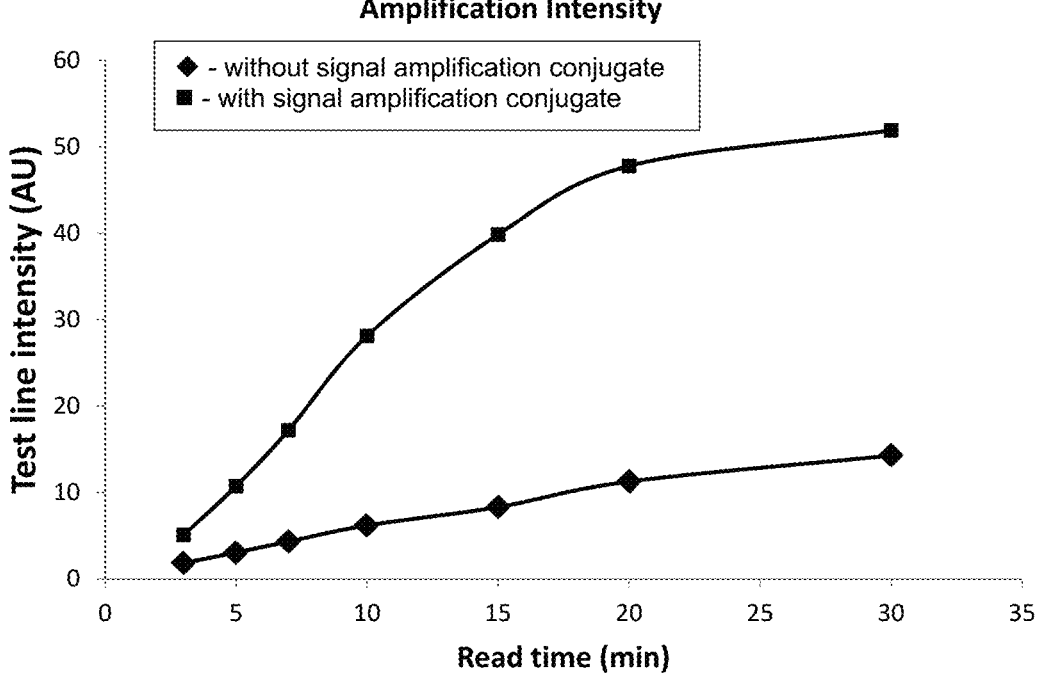
FIG. 4 illustrates results of a signal amplification reaction on a lateral flow device performed according to the present disclosure, indicating signal intensity as a function of read time for a control signal (absence of a signal-amplification conjugate—♦) and a test signal (with signal-amplification conjugate—■).

Lateral flow assays as prepared in Example 1 were contacted with samples containing low concentration Flu A. In this non-limiting example, the Flu A antigen was a dilution of recombinant Flu A nucleoprotein expressed in *E. coli* and was applied as a crude cell lysis. As a control, a lateral flow assay prepared as in Example 1, but lacking signal-amplification conjugate was used. The sample having Flu A was added to the sample well of the lateral flow device and the control lateral flow device. The generated signal was measured at various time points, as shown in FIG. 4, and in Table 1.

TABLE 1

Change in Signal Over Time

| Time (minutes) | Control Signal Intensity (without amplification conjugate) | Test Signal Intensity (with amplification conjugate) |
|---|---|---|
| 3 | 1.83 | 5.087 |
| 5 | 3.05 | 10.73 |
| 7 | 4.32 | 17.2 |
| 10 | 6.19 | 28.12 |
| 15 | 8.31 | 39.85 |
| 20 | 11.3 | 47.79 |
| 30 | 14.3 | 51.91 |

Samples that did not contain analyte of interest were also applied to lateral flow assays that were prepared with various amounts of signal-amplification conjugate according to the present disclosure. Specifically, amounts of 0.5, 1, 1.5, and 3 μL of signal-amplification conjugate was deposited on the test strip and compared to a control strip, with readings obtained at 10 minutes and 20 minutes. The results are shown in Table 2, with each time point measured in duplicate. The samples that did not contain analyte of interest were deposited on the assay test strips to verify that a signal will not be generated at the test line when there is no analyte of interest present in the sample. As shown in Table 2 below, the signal at the test line remained negative (0 AU or substantially 0 AU signal intensity was measured at the test line) for all samples not containing analyte of interest. Any signal below 1 AU can be considered as system noise and therefore equivalent to a measurement of 0 AU. Further, as shown in Table 2 below, the intensity of system noise measurements did not increase with increasing amounts of signal-amplification conjugate. Without being bound to any particular theory, it is believed that the signal-amplification conjugate does not amplify a signal in the absence of analyte of interest because there is no initial signal to amplify (in other words, no sandwich structures were formed on the test line due to absence of analyte in the sample, and therefore no sandwich structures were present to generate a signal to be amplified by the signal-amplification conjugate).

TABLE 2

Signals Generated When Sample Applied to Test Strip in the Absence of Analyte of Interest

| Time (minutes) | Amount of Signal-Amplification Conjugate (μL) on Test Strip | Test Signal Intensity (with signal-amplification conjugate)* |
|---|---|---|
| 10 | 0.5 | 0, 0.66 |
| | 1 | 0, 1.18 |
| | 1.5 | 0.52, 0.49 |
| | 3 | 0.49, 0 |
| 20 | 0.5 | 0, 0 |
| | 1 | 0, 1.08 |
| | 1.5 | 0.74, 0.56 |
| | 3 | 0, 0.77 |

*Each reading shows two values, as each was performed in duplicate.

Figure 5:
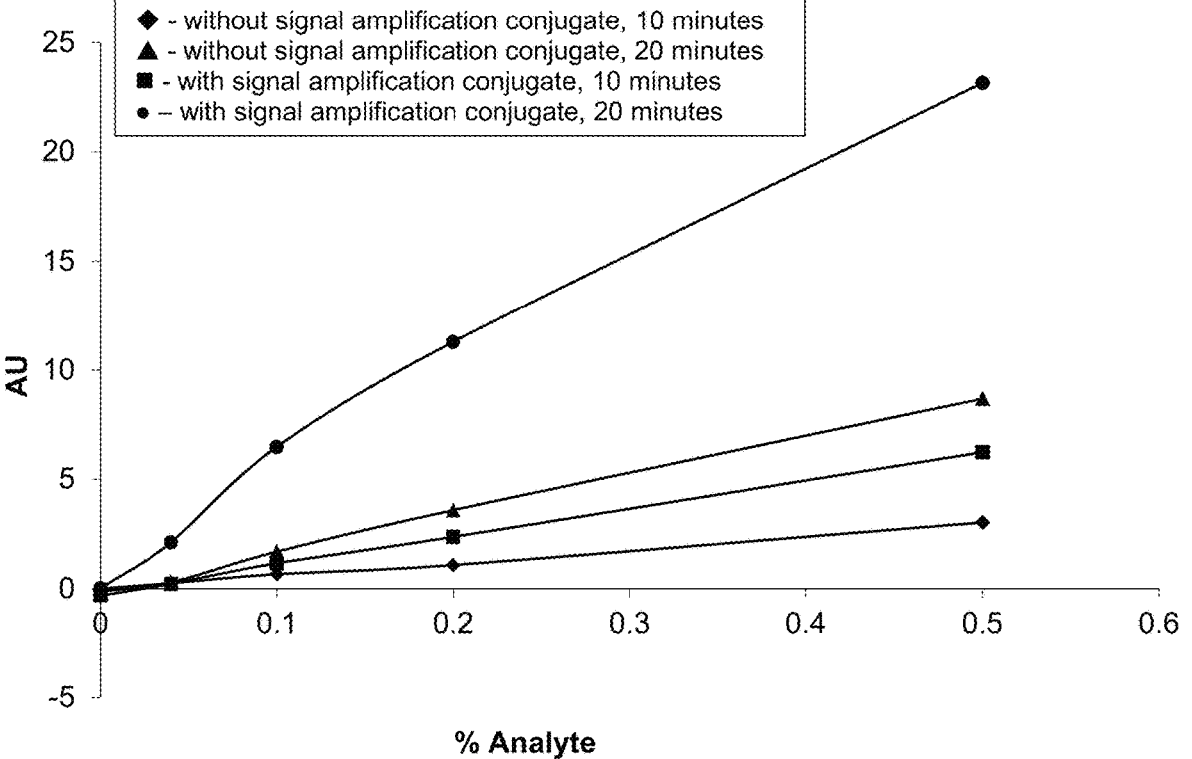
FIG. 5 illustrates results of a signal-amplification reaction on a lateral flow device performed according to the present disclosure, indicating signal intensity as a function of analyte concentration, including a control signal of an assay performed without a signal-amplification conjugate after 10 minutes (♦) and 20 minutes (▲), and a test signal with a signal-amplification conjugate after 10 minutes (■) and 20 minutes (●).

Finally, the amount of Flu A was varied in the samples prior to placement on the lateral flow devices. Specifically, samples having Flu A in an amount of 0%, 0.04%, 0.1%, 0.2%, and 0.5% (expressed in terms of percent of antigen concentration in the sample) were prepared, and the samples deposited onto the lateral flow device and a control lateral flow device without any signal-amplification conjugate. The signal intensity was read at 10 minutes and 20 minutes. The results are shown in FIG. 5 and in Table 3.

TABLE 3

Signal Intensity with Different Amounts of Analyte of Interest

| Time (minutes) | Amount of Flu A (%) | Control Signal Intensity (no signal-amplification conjugate) | Test Signal Intensity (with signal-amplification conjugate) |
|---|---|---|---|
| 10 | 0 | 0 | −0.13 |
| | 0.04 | 0.25 | 0.29 |
| | 0.1 | 0.66 | 1.69 |
| | 0.2 | 1.08 | 3.59 |
| | 0.5 | 3.03 | 8.69 |
| 20 | 0 | −0.32 | 0.02 |
| | 0.04 | 0.22 | 2.12 |
| | 0.1 | 1.16 | 6.48 |
| | 0.2 | 2.37 | 11.29 |
| | 0.5 | 6.24 | 23.16 |

Advantageously, the lateral flow assay according to the present disclosure amplifies a signal of analyte present in a sample at a low concentration, such as a concentration below a detection limit, thereby allowing reliable measurement of analyte present in a sample at low concentration. In addition to determine the presence of an analyte of interest in a sample, embodiments of the present disclosure can also be used to quantitate the amount of analyte of interest present in a sample. For example, solutions having known quantities of analyte of interest can be applied to assay test strips prepared in accordance with embodiments of the present disclosure. A measurement system can measure the intensity of signals generated by the strips and a dose response curve can be developed using this data. Following a test event using a test strip prepared according to embodiments of the present disclosure, a measurement system can measure the signal generated by the test strip and compare this test signal to the signals plotted in the dose response curve to determine a quantity of analyte of interest in the test sample. It will be understood that other methods of quantitating the amount of analyte of interest are possible using embodiments of the present disclosure.

Figure 6:
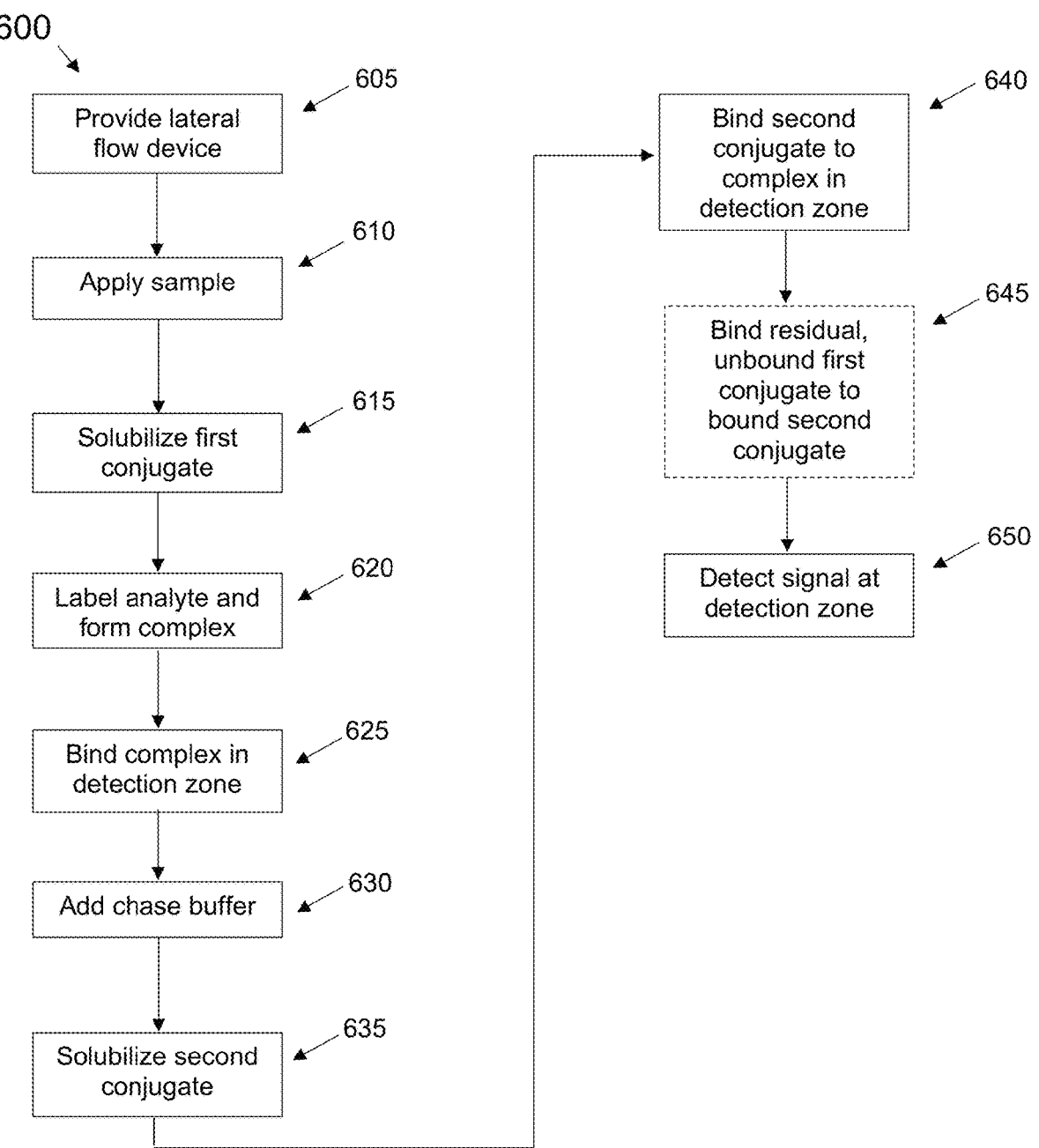
FIG. 6 illustrates a flow diagram for an example method of using lateral flow assays to detect an analyte of interest in a sample at low concentration.

Methods of Detecting an Analyte of Interest in a Sample using the Lateral Flow Assays According to the Present Disclosure FIG. 6 illustrates an example method 600 of using lateral flow assays to detect an analyte of interest in a sample at low concentration according to the present disclosure. The method 600 begins at step 605 in which a lateral flow assay as described herein is provided. At step 610, a sample is applied to a sample well of the lateral flow device.

In some embodiments, applying the sample at the sample well includes contacting a sample with a lateral flow assay. A sample may contact a lateral flow assay by introducing a sample to a sample well by external application, as with a dropper or other applicator. In some embodiments, a sample reservoir may be directly immersed in the sample, such as when a test strip is dipped into a container holding a sample. In some embodiments, a sample may be poured, dripped, sprayed, placed, or otherwise contacted with the sample reservoir.

The method next moves to step 615, in which application of the sample at the sample well solubilizes analyte-specific conjugate ("first conjugate") present at the sample receiving zone or in a first conjugate zone downstream of the sample receiving zone. The analyte-specific conjugate may include a first label, a first binding partner, and an agent that specifically binds an analyte of interest. As described above, the device may include a second analyte-specific conjugate that includes a label, a binding partner, and an agent that specifically binds a second analyte of interest, and the device may also include a third analyte-specific conjugate that includes a label, a binding partner, and an agent that specifically binds a third analyte of interest, or additional analyte-specific conjugates, depending on the number of analytes to be analyzed. In some embodiments, an analyte-specific conjugate may not include a binding partner, as a specific analyte of interest may not require amplification due to the expected or typical concentration of the specific analyte of interest in the sample.

The analyte-specific conjugate (or more than one analyte-specific conjugate, if such is the case) can be integrated on the sample receiving zone by physical or chemical bonds. The sample solubilizes the analyte-specific conjugate after the sample is added to the sample well, releasing the bonds holding the analyte-specific conjugate to the conjugate pad.

Moving next to step 620, analyte of interest (if present in the sample) is labeled with the analyte-specific conjugate. The analyte-specific conjugate binds to the analyte of interest, if present in the sample, forming a complex. It will be understood that step 615 and step 620 may occur at substantially the same time.

The method next moves to step 625, in which complex moves along the fluid flow path of the assay test device and is bound to immobilized capture agent at a detection zone of the lateral flow assay, forming a sandwich structure. It will also be understood that implementations of the present disclosure can form a sandwich structure in the detection zone in many different ways. For example, steps 615, 620, and 625 may be replaced with a step 615A in which analyte of interest and analyte-specific conjugate flow separately to the detection zone, analyte of interest binds to the immobilized capture agent in the detection zone, then analyte-specific conjugate binds to the now-bound analyte of interest, forming an antibody-analyte-antibody-first label structure, typically referred to as a sandwich.

After binding the complex to immobilized capture agent (or otherwise forming a sandwich structure), the method next moves to step 630, where a buffer is applied to the buffer well (or other suitable location) of the device. At step 635, the buffer solubilizes signal-amplification conjugate ("second conjugate") present at or located downstream of the buffer receiving zone. The signal-amplification conjugate includes a second label and a second binding partner that binds specifically to the first binding partner of the analyte-specific conjugate. The signal-amplification conjugate can be integrated on the buffer receiving zone (or other suitable location) by physical or chemical bonds. The buffer solubilizes the signal-amplification conjugate after the buffer is added to the buffer well, releasing the bonds holding the signal-amplification conjugate to the conjugate pad of the buffer receiving zone (or other suitable location). It will be understood that steps 630 and 635 may be replaced with an alternative method to add signal-amplification conjugate to the lateral flow assay.

The method next moves to step 640, in which the signal-amplification conjugate flows with the buffer to the detection zone. In the detection zone, the second binding partner forms a binding pair with the first binding partner of the analyte-specific conjugate in the complex bound to capture agent in the detection zone. As described above, this first binding interaction between the signal-amplification conjugate and the complex bound to capture agent in the detection zone can amplify a signal generated in the detection zone to a level that exceeds a threshold detection level. Accordingly, in some example implementations, the method next moves to step 650 where the amplified signal is detected at the detection zone.

Embodiments of methods according to the present disclosure can also include follow-on binding interactions as described above. A chain reaction of binding events occurs in accordance with the present disclosure, and a series of first binding pair and second binding pair interactions cause an accumulation of analyte-specific conjugate and signal-amplification conjugate to form in the detection zone. The accumulation of conjugate at the detection zone results in amplification of a signal generated at the detection zone, in some cases an exponential amplification of the signal. This chain reaction of binding events is illustrated in step 645 of FIG. 6, where residual, unbound first conjugate that is present in the detection zone binds to signal-amplification conjugate that has become bound to complex in the detection zone.

Moving next to step 650, the method includes detecting a signal generated at the detection zone. The detection zone may include a capture zone for capturing each complex (where more than one analyte of interest is to be detected and/or quantified). For example, the detection zone may include a first capture zone for capturing a first complex, a second capture zone for capturing a second complex, and a third capture zone for capturing a third complex. A first immobilized capture agent at the first capture zone binds first analyte (if present) and the first complex. When first complex binds to first immobilized capture agent at the first capture zone, and signal-amplification conjugate binds thereto, a first amplified signal is detected. The first amplified signal may include an optical signal as described herein. The signal generated at the detection zone can be detected using any suitable measurement system at step 650, including but not limited to visual inspection of the device and optical detection using an optical reader. The signal detected at step 650 can be correlated to the presence, absence, or quantity of the analyte of interest in the sample.

In some embodiments, the sample is obtained from a source, including an environmental or biological source. In some embodiments, the sample is suspected of having one or more analytes of interest, including one or more analytes of interest present in a low concentration, such as a concentration below a detection limit of a measurement system. In some embodiments, the sample is not suspected of having any analytes of interest. In some embodiments, a sample is obtained and analyzed for verification of the absence or presence of a plurality of analytes. In some embodiments, the fluid sample is blood or plasma. In some embodiments, the fluid sample is applied in an amount of 50 to 100 μL.

In some embodiments, the detected signal is an optical signal, a fluorescent signal, or a magnetic signal.

Example Test Systems Including Lateral Flow Assays According to the Present Disclosure Lateral flow assay test systems described herein can include a lateral flow assay test device (such as but not limited to a test strip), a system housing including a port configured to receive all or a portion of the test device, a reader including a light source and a light detector, a data analyzer, and combinations thereof. A system housing may be made of any one of a wide variety of materials, including plastic, metal, or composite materials. The system housing forms a protective enclosure for components of the diagnostic test system. The system housing also defines a receptacle that mechanically registers the test strip with respect to the reader. The receptacle may be designed to receive any one of a wide variety of different types of test strips. In some embodiments, the system housing is a portable device that allows for the ability to perform a lateral flow assay in a variety of environments, including on the bench, in the field, in the home, or in a facility for domestic, commercial, or environmental applications.

A reader may include one or more optoelectronic components for optically inspecting the exposed areas of the detection zone of the test strip, and capable of detecting multiple capture zones within the detection zone. In some implementations, the reader includes at least one light source and at least one light detector. In some embodiments, the light source may include a semiconductor light-emitting diode and the light detector may include a semiconductor photodiode. Depending on the nature of the label that is used by the test strip, the light source may be designed to emit light within a particular wavelength range or light with a particular polarization. For example, if the label is a fluorescent label, such as a quantum dot, the light source would be designed to illuminate the exposed areas of the capture zone of the test strip with light in a wavelength range that induces fluorescent emission from the label. Similarly, the light detector may be designed to selectively capture light from the exposed areas of the capture zone. For example, if the label is a fluorescent label, the light detector would be designed to selectively capture light within the wavelength range of the fluorescent light emitted by the label or with light of a particular polarization. On the other hand, if the label is a reflective-type label, the light detector would be designed to selectively capture light within the wavelength range of the light emitted by the light source. To these ends, the light detector may include one or more optical filters that define the wavelength ranges or polarizations axes of the captured light. A signal from a label can be analyzed, using visual observation or a spectrophotometer to detect color from a chromogenic substrate; a radiation counter to detect radiation, such as a gamma counter for detection of $^{125}$I; or a fluorometer to detect fluorescence in the presence of light of a certain wavelength. Where an enzyme-linked assay is used, quantitative analysis of the amount of an analyte of interest can be performed using a spectrophotometer. Lateral flow assays described herein can be automated or performed robotically, if desired, and the signal from multiple samples can be detected simultaneously. Furthermore, multiple signals can be detected for a plurality of analytes of interest, including when the label for each analyte of interest is the same or different.

The data analyzer processes the signal measurements that are obtained by the reader. In general, the data analyzer may be implemented in any computing or processing environment, including in digital electronic circuitry or in computer hardware, firmware, or software. In some embodiments, the data analyzer includes a processor (e.g., a microcontroller, a microprocessor, or ASIC) and an analog-to-digital converter. The data analyzer can be incorporated within the housing of the diagnostic test system. In other embodiments, the data analyzer is located in a separate device, such as a computer, that may communicate with the diagnostic test system over a wired or wireless connection. The data analyzer may also include circuits for transfer of results via a wireless connection to an external source for data analysis or for reviewing the results.

In general, the results indicator may include any one of a wide variety of different mechanisms for indicating one or more results of an assay test. In some implementations, the results indicator includes one or more lights (e.g., light-emitting diodes) that are activated to indicate, for example, the completion of the assay test. In other implementations, the results indicator includes an alphanumeric display (e.g., a two or three character light-emitting diode array) for presenting assay test results.

Test systems described herein can include a power supply that supplies power to the active components of the diagnostic test system, including the reader, the data analyzer, and the results indicator. The power supply may be implemented by, for example, a replaceable battery or a rechargeable battery. In other embodiments, the diagnostic test system may be powered by an external host device (e.g., a computer connected by a USB cable).

Features of Example Lateral Flow Devices

Lateral flow devices described herein include a device housing. The housing of any of the lateral flow devices described herein, including the top housing or the base housing, may be made with any suitable material, including, for example, vinyl, nylon, polyvinyl chloride, polypropylene, polystyrene, polyethylene, polycarbonates, polysulfanes, polyesters, urethanes, or epoxies. The housing may be prepared by any suitable method, including, for example, by injection molding, compression molding, transfer molding, blow molding, extrusion molding, foam molding, thermoform molding, casting, layer deposition, or printing.

Lateral flow devices described herein can include a sample well where a fluid sample is introduced to a test strip, such as but not limited to an immunochromatographic test strip present in a lateral flow device. In one example, the sample may be introduced to the sample well by external application, as with a dropper or other applicator. The sample may be poured or expressed onto the sample well. In another example, the sample well may be directly immersed in the sample, such as when a test strip is dipped into a container holding a sample.

Lateral flow devices described herein can include a buffer well where a buffer is introduced to a test strip, such as but not limited to an immunochromatographic test strip present in a lateral flow device. In one example, the buffer may be introduced to the buffer well by external application, as with a dropper or other applicator. The buffer may be poured or expressed onto the buffer well. In another example, the buffer well may be directly immersed in the buffer, such as when a test strip is dipped into a container holding a buffer.

Lateral flow devices described herein can include a solid support or substrate. Suitable solid supports include but are not limited to nitrocellulose, the walls of wells of a reaction tray, multi-well plates, test tubes, polystyrene beads, magnetic beads, membranes, and microparticles (such as latex particles). Any suitable porous material with sufficient porosity to allow access by analyte-specific conjugate and signal-amplification conjugate and a suitable surface affinity to immobilize capture agent can be used in lateral flow devices described herein. For example, the porous structure of nitrocellulose has excellent absorption and adsorption qualities for a wide variety of agents, for instance, immobilized capture agents. Nylon possesses similar characteristics and is also suitable. Microporous structures are useful, as are materials with gel structure in the hydrated state.

Further examples of useful solid supports include: natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

Lateral flow devices described herein can include porous solid supports, such as nitrocellulose, in the form of sheets or strips. The thickness of such sheets or strips may vary within wide limits, for example, from about 0.01 to 0.5 mm, from about 0.02 to 0.45 mm, from about 0.05 to 0.3 mm, from about 0.075 to 0.25 mm, from about 0.1 to 0.2 mm, or from about 0.11 to 0.15 mm. The pore size of such sheets or strips may similarly vary within wide limits, for example from about 0.025 to 15 microns, or more specifically from about 0.1 to 3 microns; however, pore size is not intended to be a limiting factor in selection of the solid support. The flow rate of a solid support, where applicable, can also vary within wide limits, for example from about 12.5 to 90 sec/cm (i.e., 50 to 300 sec/4 cm), about 22.5 to 62.5 sec/cm (i.e., 90 to 250 sec/4 cm), about 25 to 62.5 sec/cm (i.e., 100 to 250 sec/4 cm), about 37.5 to 62.5 sec/cm (i.e., 150 to 250 sec/4 cm), or about 50 to 62.5 sec/cm (i.e., 200 to 250 sec/4 cm). In specific embodiments of devices described herein, the flow rate is about 35 sec/cm (i.e., 140 sec/4 cm). In other specific embodiments of devices described herein, the flow rate is about 37.5 sec/cm (i.e., 150 sec/4 cm).

The surface of a solid support may be activated by chemical processes that cause covalent linkage of an agent (e.g., an immobilized conjugate) to the support. As described below, the solid support can include a conjugate pad. Many other suitable methods may be used for immobilizing an agent (e.g., an immobilized capture agent) to a solid support including, without limitation, ionic interactions, hydrophobic interactions, covalent interactions and the like.

Except as otherwise physically constrained, a solid support may be used in any suitable shapes, such as films, sheets, strips, or plates, or it may be coated onto or bonded or laminated to appropriate inert carriers, such as paper, glass, plastic films, or fabrics.

Lateral flow devices described herein can include a conjugate pad, such as a membrane or other type of material that includes a capture agent. The conjugate pad can be a cellulose acetate, cellulose nitrate, polyamide, polycarbonate, glass fiber, membrane, polyethersulfone, regenerated cellulose (RC), polytetra-fluorethylene, (PTFE), Polyester (e.g. Polyethylene Terephthalate), Polycarbonate (e.g., 4,4-hydroxy-diphenyl-2,2'-propane), Aluminum Oxide, Mixed Cellulose Ester (e.g., mixture of cellulose acetate and cellulose nitrate), Nylon (e.g., Polyamide, Hexamethylenediamine, and Nylon 66), Polypropylene, PVDF, High Density Polyethylene (HDPE)+nucleating agent "aluminum dibenzoate" (DBS) (e.g. 80 u 0.024 HDPE DBS (Porex)), and HDPE.

Lateral flow devices described herein are used for low sensitivity samples, such as samples having low concentration of analyte or having a typical concentration of analyte but in a low volume of sample. "Sensitivity" refers to the proportion of actual positives that are correctly identified as such (for example, the percentage of infected, latent, or symptomatic subjects who are correctly identified as having a condition). Sensitivity may be calculated as the number of true positives divided by the sum of the number of true positives and the number of false negatives.

Lateral flow devices described herein can accurately measure a plurality of analytes of interest in many different kinds of samples. Samples can include a specimen or culture obtained from any source, as well as biological and environmental samples. Biological samples may be obtained from animals (including humans) and encompass fluids, solids, tissues, and gases. A sample may be processed prior to being applied to a lateral flow device of the present disclosure. In a first non-limiting example, a whole blood sample can be processed to obtain plasma or serum, and the plasma or serum can be applied to a lateral flow device according to the present disclosure. In a second non-limiting example, a sample containing cells is processed using one or more sample preparation steps, such as but not limited to a cell lysis step to release intracellular proteins for detection. The processed sample can be applied to a lateral flow device according to the present disclosure. Biological samples include urine, saliva, and blood products, such as plasma, serum and the like. Such examples are not however to be construed as limiting the sample types applicable to the present disclosure.

Lateral flow devices described herein can include a label. Labels can take many different forms, including a molecule or composition bound or capable of being bound to an analyte, analyte analog, detector reagent, or binding partner that is detectable by spectroscopic, photochemical, biochemical, immunochemical, electrical, optical or chemical means. Examples of labels include enzymes, colloidal gold particles (also referred to as gold nanoparticles), colored latex particles, radioactive isotopes, co-factors, ligands, chemiluminescent or fluorescent agents, protein-adsorbed silver particles, protein-adsorbed iron particles, protein-adsorbed copper particles, protein-adsorbed selenium particles, protein-adsorbed sulfur particles, protein-adsorbed tellurium particles, protein-adsorbed carbon particles, and protein-coupled dye sacs. The attachment of a compound (e.g., a detector reagent) to a label can be through covalent bonds, adsorption processes, hydrophobic and/or electrostatic bonds, as in chelates and the like, or combinations of these bonds and interactions and/or may involve a linking group.

The term "specific binding partner" or "binding partner" refers to a member of a pair of molecules that interacts by means of specific, noncovalent interactions that depend on the three-dimensional structures of the molecules involved. Typical pairs of specific binding partners include antigen/antibody, hapten/antibody, hormone/receptor, nucleic acid strand/complementary nucleic acid strand, substrate/enzyme, inhibitor/enzyme, carbohydrate/lectin, biotin/(strept) avidin, receptor/ligands, and virus/cellular receptor, or various combinations thereof.

As used herein, the terms "immunoglobulin" or "antibody" refer to proteins that bind a specific antigen. Immunoglobulins include, but are not limited to, polyclonal, monoclonal, chimeric, and humanized antibodies, Fab fragments, F(ab')2 fragments, and includes immunoglobulins of the following classes: IgG, IgA, IgM, IgD, IgE, and secreted immunoglobulins (sIg). Immunoglobulins generally comprise two identical heavy chains and two light chains. However, the terms "antibody" and "immunoglobulin" also encompass single chain antibodies and two chain antibodies. The term antibody as used herein refers to the antibody as a whole or any fragment thereof, including binding fragments thereof. Thus, it is contemplated that when referring to a labeled antibody that specifically binds analyte of interest, the term refers to a labeled antibody or fragment thereof that specifically binds an analyte of interest. Similarly, when referring to a capture agent or antibody, the term refers to a capture antibody or fragment thereof that specifically binds to the analyte of interest.

Antibodies in lateral flow devices, test systems, and methods according to the present disclosure can include a polyclonal antibody. Polyclonal antibodies for measuring any of the analytes of interest disclosed herein include without limitation antibodies that were produced from sera by active immunization of one or more of the following: Rabbit, Goat, Sheep, Chicken, Duck, Guinea Pig, Mouse, Donkey, Camel, Rat, and Horse. Antibodies in lateral flow devices, test systems, and methods according to the present disclosure can include a monoclonal antibody. Antibodies for binding to analytes of interest are known in the art or may be readily developed by methods known in the art.

Lateral flow devices according to the present disclosure include an immobilized capture agent. An immobilized capture agent includes an agent that is capable of binding to an analyte, including a free (unlabeled) analyte and/or a labeled analyte (such as analyte bound to an analyte-specific conjugate, as described herein). An immobilized capture agent includes an unlabeled specific binding partner that is specific for (i) a analyte of interest bound by the analyte-specific conjugate, (ii) free analyte, or for (iii) an ancillary specific binding partner, which itself is specific for the analyte, as in an indirect assay. As used herein, an "ancillary specific binding partner" is a specific binding partner that binds to the specific binding partner of an analyte. For example, an ancillary specific binding partner may include an antibody specific for another antibody, for example, goat anti-human antibody.

Lateral flow devices described herein can include a "detection area" or "detection zone" that is an area that includes one or more capture area or capture zone and that is a region where a detectable signal may be detected. Lateral flow devices described herein can include a "capture zone" or "capture area" that is a region of the lateral flow device where the capture agent is immobilized. Lateral flow devices described herein may include more than one capture zone. In some cases, a different capture agent will be immobilized in different capture zones (such as a first immobilized capture agent at a first capture zone and a second immobilized capture agent at a second capture zone). Multiple capture zones may have any orientation with respect to each other on the lateral flow substrate; for example, a first capture zone may be distal or proximal to a second (or other) capture zone along the path of fluid flow and vice versa. Alternatively, a first capture zone and a second (or other) capture zone may be aligned along an axis perpendicular to the path of fluid flow such that fluid contacts the capture zones at the same time or about the same time.

Lateral flow devices according to the present disclosure include immobilized capture agents that are immobilized such that movement of the immobilized capture agents is restricted during normal operation of the lateral flow device. For example, movement of an immobilized capture agent is restricted before and after a fluid sample is applied to the lateral flow device. Immobilization of immobilized capture agent can be accomplished by physical means such as barriers, electrostatic interactions, hydrogen bonding, bioaffinity, covalent interactions, or combinations thereof.

Lateral flow devices according to the present disclosure can measure a biologic. A biologic includes chemical or biochemical compounds produced by a living organism, including a prokaryotic cell line, a eukaryotic cell line, a mammalian cell line, a microbial cell line, an insect cell line, a plant cell line, a mixed cell line, a naturally occurring cell line, or a synthetically engineered cell line. A biologic can include large macromolecules such as proteins, polysaccharides, lipids, and nucleic acids, as well as small molecules such as primary metabolites, secondary metabolites, and natural products.

It is to be understood that the description, specific examples and data, while indicating exemplary embodiments, are given by way of illustration and are not intended to limit the various embodiments of the present disclosure. Various changes and modifications within the present disclosure will become apparent to the skilled artisan from the description and data contained herein, and thus are considered part of the various embodiments of this disclosure.

What is claimed is:

1. A lateral flow assay device for detecting an analyte of interest in a sample comprising:
   a first conjugate comprising a first label, an agent configured to specifically bind to the analyte of interest, and a first binding partner;
   a second conjugate upstream of the first conjugate along a fluid flow path of the lateral flow assay device, wherein the second conjugate comprises a second label and a second binding partner configured to specifically bind to the first binding partner, wherein the second binding partner is an antibody against the first binding partner, and wherein the first label and the second label are the same; and
   a detection zone downstream of the first conjugate and the second conjugate along the fluid flow path of the lateral flow assay device, the detection zone comprising an immobilized capture agent that specifically binds the analyte of interest.

2. The assay device of claim 1, wherein the first conjugate is present in a sample receiving zone of the lateral flow assay device, or wherein the first conjugate is present in a first conjugate zone downstream of the sample receiving zone.

3. The assay device of claim 2, wherein the second conjugate is present in a buffer receiving zone upstream of the sample receiving zone, or wherein the second conjugate is present in a second conjugate zone downstream of the buffer receiving zone and upstream of the sample receiving zone.

4. The assay device of claim 3, further comprising:
a housing comprising a sample receiving well positioned laterally above or upstream of the first conjugate, a buffer well positioned laterally above or upstream of the second conjugate zone, and a read window accessible to the detection zone.

5. The assay device of claim 4, wherein the buffer well, the second conjugate zone, the sample receiving well, and the first conjugate zone are spatially separated along the fluid flow path of the lateral flow assay device.

6. The assay device of claim 1, wherein the first conjugate is configured to be solubilized and mobilized to the detection zone upon application of a fluid sample to the lateral flow assay device.

7. The assay device of claim 6, wherein the second conjugate is configured to be solubilized and mobilized to the detection zone after the first conjugate mobilizes to the detection zone.

8. The assay device of claim 1, wherein the agent configured to specifically bind to an analyte of interest is an antibody or antibody binding fragment that specifically binds the analyte of interest.

9. The assay device of claim 1, wherein the first binding partner comprises biotin and the second binding partner comprises anti-biotin antibody.

10. The assay device of claim 1, wherein the analyte of interest is a biological or environmental substance of interest.

11. The assay device of claim 1, wherein the analyte of interest is an influenza virus.

12. The assay device of claim 11, wherein the influenza virus is influenza A virus, influenza B virus, or influenza C virus.

13. The assay device of claim 1, wherein the immobilized capture agent is an antibody or antibody binding fragment that specifically binds the analyte of interest.

14. The assay device of claim 1, wherein the fluid flow path comprises a test strip, which comprises a nitrocellulose membrane.

15. The assay device of claim 1, further comprising a control zone comprising immobilized capture agent that specifically binds the first conjugate.

16. The assay device of claim 1, wherein the first and second label is selected from the group consisting of a metal nanoparticle, a blue latex bead, a metal nanoparticle, a colored latex particle, a colored latex bead, a magnetic particle, a carbon nanoparticle, a quantum dot, an up converting phosphor, an organic fluorophore, a textile dye, an enzyme, and a liposome.

17. The assay device of claim 1, wherein the first label and the second label comprise a gold nanoparticle.

18. The assay device of claim 1, wherein the first label and the second label are configured to generate an optical signal, a fluorescent signal, or a magnetic signal.

19. A method of detecting an analyte of interest in a sample, comprising:
applying a sample to a lateral flow assay device comprising
a first conjugate comprising a first label, an agent configured to specifically bind to the analyte of interest, and a first binding partner;
a second conjugate upstream of the first conjugate along a fluid flow path of the lateral flow assay device, wherein the second conjugate comprises a second label and a second binding partner configured to specifically bind to the first binding partner, wherein the second binding partner is an antibody against the first binding partner, and wherein the first label and the second label are the same; and
a detection zone downstream of the first conjugate and the second conjugate along the fluid flow path of the lateral flow assay device, the detection zone comprising an immobilized capture agent that specifically binds the analyte of interest;
binding a complex to the immobilized capture agent in the detection zone, wherein the complex comprises analyte of interest bound to the first conjugate;
after binding the complex, releasing the second conjugate to flow along the fluid flow path of the lateral flow assay device;
binding the second conjugate to the complex bound in the detection zone; and
detecting a signal generated by the complex and the second conjugate bound in the detection zone, thereby detecting analyte of interest in the sample.

20. The method of claim 19, further comprising binding first conjugate that has not bound to the analyte of interest to the second conjugate bound to the complex in the detection zone.

21. The method of claim 19, wherein the first label and the second label are configured to generate an optical signal, a fluorescent signal, or a magnetic signal.

22. The method of claim 19, wherein the second conjugate is released 5 seconds, 10 seconds, 15 seconds, 20 seconds, 25 second, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, or 10 minutes after applying a sample to the lateral flow device.

23. The method of claim 19, wherein binding a complex to the immobilized capture agent in the detection zone comprises:
labeling the analyte of interest with the first conjugate to form a complex; and
binding the complex to the immobilized capture agent in the detection zone.

24. The method of claim 19, wherein releasing the second conjugate comprises applying a buffer solution to the second conjugate or to a position on the lateral flow assay device upstream of the second conjugate.

25. The method of claim 24, wherein applying a buffer solution comprises pouring a buffer solution in a buffer receiving well positioned laterally above or upstream of the second conjugate.

* * * * *